United States Patent
Masciadri et al.

(10) Patent No.: US 6,686,352 B2
(45) Date of Patent: Feb. 3, 2004

(54) SUBSTITUTED IMIDAZO [1,5-A] PYRIMIDO [5,4-D] [1] BENZAZEPINE DERIVATIVES

(75) Inventors: Raffaello Masciadri, Basel (CH); Andrew William Thomas, Birsfelden (CH); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/118,584

(22) Filed: Apr. 9, 2002

(65) Prior Publication Data

US 2003/0055042 A1 Mar. 20, 2003

(30) Foreign Application Priority Data

May 18, 2001 (EP) .............................. 01112222

(51) Int. Cl.⁷ .................... A61K 31/55; A61P 25/28; C07D 487/12
(52) U.S. Cl. .................. 514/214.02; 540/578
(58) Field of Search .................. 514/214.02; 540/578

(56) References Cited

U.S. PATENT DOCUMENTS 5,387,585 A  2/1995  Borer et al. ............. 514/219

FOREIGN PATENT DOCUMENTS

| EP | 0 519 307 | 12/1992 |
| FR | 2783828 | 3/2000 |
| WO | WO 01 34603 | 5/2001 |
| WO | WO 02 40487 | 5/2002 |

OTHER PUBLICATIONS

McNamara et al., *Psychobiology*, vol. 21(2), pp. 101–108 (1993).
Walser et al., *J. Heterocyclic Chem.*, vol. 15, pp. 577–583 (1978).
Ning etal., *J.Org. Chem.*, vol. 41, No. 16, pp. 2724–2727 (1976).
Ning et al., *J. Org. Chem.*, vol. 41, pp. 2720–2724 (1976).
Goel et al., *Synthesis* pp.162–164 (1987).
Castle et al., *J. Heterocyclic Chem.*, vol. 2, pp. 459–462 (1965).
Rene Borer et al., *Heterocycles*, vol. 39, No. 2, pp. 693–721 (1994).
Thomas et al., *Nucleotides and Nucleosides*, vol. 13, pp.309–323 (1994).
Bamberger, J. Liebigs. Ann. Chem., pp. 289–362 (1899).
Wang et al., *CNS Drug Reviews*, Vol. 5, No. 2, pp. 125–144 (1999).

*Primary Examiner*—Brenda Coleman
(74) *Attorney, Agent, or Firm*—George W. Johnston; Patricia S. Rocha-Tramaloni; Kimberly J. Prior

(57) ABSTRACT

The present invention is a compound of formula

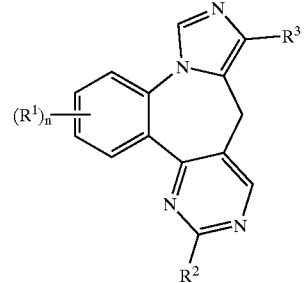

I wherein
  $R^1$ is halogen or lower alkyl;
  $R^2$ is hydrogen, lower alkyl, cycloalkyl, —$(CH_2)_m$-phenyl, wherein the phenyl ring may be substituted by lower alkoxy, or is —$(CH_2)_m$-indolyl;
  $R^3$ is —C(O)O-lower alkyl, —C(O)OH, or a five membered heteroaromatic group, which rings may be substituted by lower alkyl or cycloalkyl;
  n is 0, 1 or 2;
  m is 0, 1 or 2;
or a pharmaceutically acceptable acid addition salt thereof. Compound I shows high affinity and selectivity for GALA A α5 receptor binding sites.

12 Claims, No Drawings

SUBSTITUTED IMIDAZO [1,5-A] PYRIMIDO [5,4-D] [1] BENZAZEPINE DERIVATIVES

FIELD OF INVENTION

The present invention is related to substituted imidazo[1,5-a]pyrimido[5,4-d][1]benzazepine derivatives of formula

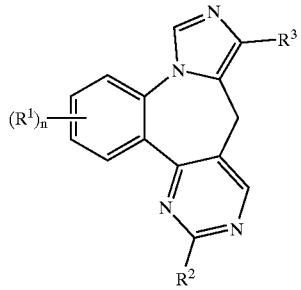

I

Compounds of formula 1 are ligands for GABA A receptors containing the α5 subunit and are therefore useful in therapy where cognition enhancement is desirable.

BACKGROUND

Receptors for the major inhibitory neurotransmitter, gamma-aminobutyric acid (GABA), are divided into two main classes: (1) GABA A receptors, which are members of the ligand-gated ion. channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding. site lies between the cc and y subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101–108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY

The present invention is a compound of formula

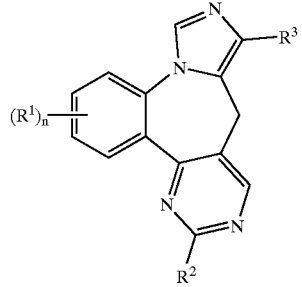

I wherein
$R^1$ is selected from the group consisting of halogen and lower alkyl;
$R^2$ is selected from the group consisting of hydrogen, lower alkyl, cycloalkyl, —$(CH_2)_m$-phenyl, —$(CH_2)_m$-phenyl substituted by lower alkoxy and —$(CH_2)_m$-indolyl;
$R^3$ is selected from the group consisting of —C(O)O-lower alkyl, —C(O)OH, a five-membered heteroaromatic group and a five-membered heteroaromatic group substituted by lower alkyl or cycloalkyl;
n is 0, 1 or 2; and
m is 0, 1 or 2;
or a pharmaceutically acceptable acid addition salt thereof
It has now been found that a compound of formula 1 shows high affinity and selectivity for GABA A α5 receptor binding sites and might be useful as a cognitive enhancer or for the treatment of cognitive disorders like Alzheimer's disease.

An object of the present invention is compounds of formula I and pharmaceutically acceptable salts thereof. A further object of the invention is the preparation of the compounds of formula I and pharmaceutically acceptable salts thereof. Pharmaceutical compositions containing a therapeutically effective amount of the compound of formula I and salts thereof and their manufacture are objects of the present invention. Another object of the invention is a method of treatment for modulating GABA A α5 receptor binding sites as a cognitive enhancer or treatment of cognitive disorders like Alzheimer's disease comprising the administration of a therapeutically effective amount of the compounds of formula I or a pharmaceutically acceptable salt. The most preferred indication in accordance with the method of treatment of the present invention is the treatment of cognitive disorders, like Alzheimer's disease.

DETAILED DESCRIPTION

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like. Preferred lower alkyl groups are groups with 1–4 carbon atoms.

The term "lower alkoxy" denotes a croup wherein the alkyl residues are as defined above, and which is attached via an oxygen atom.

The term "halogen" denotes chlorine, iodine, fluorine and bromine.

The term "cycloalkyl" denotes a cyclic alkyl ring, having from 3 to 7 carbon ring atoms, for example, cyclopropyl, cyclopentyl or cyclohexyl.

The term "five-membered heteroaromatic group" denotes, for example 1,2,4-oxadiazoles, furyl, pyrrolyl, thienyl, imidazolyl, pyrazolyl, isothiazolyl, isoxazolyl and the like. Preferred are 1,2,4-oxadiazolyl and isoxazolyl groups.

The term "pharmaceutically acceptable acid addition salts" embraces salts with pharmaceutically acceptable inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Exemplary preferred are compounds, which have a binding activity (Ki) of lower 15 nM and are selective for GABA A α5 subunits and are relatively free of activity at GABA A α1, α2 and α3 receptor binding sites.

Preferred compounds of formula I are those, in which $R^3$ is the group —C(O)O-lower alkyl. Exemplary preferred are compounds of this group, wherein $R^1$ is hydrogen and $R^2$ is as described above, for example compounds selected from the group consisting of:

9H-imidazo[1,5-a]pyrimido[5,4-d][1]benzazepine-10-carboxylic acid ethyl ester,
6-propyl-9H-imidazo[1,5-a]pyrimido[5,4-d][1]benzazepine-10-carboxylic acid ethyl ester,
6-(1-methylethyl)-9H-imidazo[1,5-a]pyrimido[5,4-d][1]benzazepine-10-carboxylic acid ethyl ester,
6-cyclopropyl-9H-imidazo[1,5-a]pyrimido[5,4-d][1]benzazepine-10-carboxylic acid ethyl ester,
6-[(4-methoxyphenyl) methyl]-9H-imidazo[1,5-a]pyrimido[5,4-d][1]benzazepine-10-carboxylic acid ethyl ester and
6-methyl-9H-imidazo[1,5-a]pyrimido[5,4-d][1]benzazepine-10-carboxylic acid ethyl ester.

Further preferred compounds of formula I are those, in which $R^3$ is the group —C(O)O-lower alkyl, $R^2$ is as described above and $R^1$ is halogen, for example compounds selected from the group consisting of:

3-fluoro-6-methyl-9H-imidazo[1,5-a]pyrimido[5,4-d][1]benzazepine-10-carboxylic acid ethyl ester,
3-fluoro-6-propyl-9H-imidazo [1,5-a]pyrimido[5,4-d][1]benzazepine-10-carboxylic acid ethyl ester,
3-fluoro-6-(1-methylethyl)-9H-imidazo[1,5-a]pyrimido[5,4-d][1]benzazepine-10-carboxylic acid ethyl ester,
6-cyclopropyl-3-fluoro-9H-imidazo[1,5-a]pyrimido[5,4-d][1]benzazepine-10-carboxylic acid ethyl ester and
3-bromo-6-methyl-9H-imidazo[1,5-a]pyrimido[5,4-d][1]benzazepine-10-carboxylic acid ethyl ester.

Further preferred compounds of formula I are those, in which $R^3$ is the group 1,2,4-oxadiazolyl or isoxazolyl, $R^2$ is lower alkyl, n is 0 or 1 and $R^1$ is halogen, for example compounds selected from the group consisting of:

10-(3-cyclopropyl-1,2,4-oxadiazol-5-yl)-6-methyl-9H-imidazo[1,5-a]pyrimido[5,4-d][1]benzazepine and
2-bromo-11-methyl-7-(5-methyl-isoxazol-3-yl)-8H-4b,6,10,12-tetraaza-dibenzo [e,g]azulene.

The present compounds of formula I and their pharmaceutically acceptable salts may be prepared by methods known in the art, for example, by processes described below, reacting a compound of formula

II

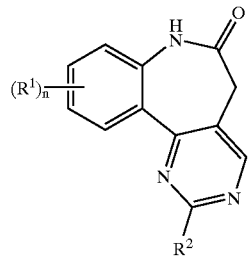

with phosphoroxychloride forming a compound of formula

III

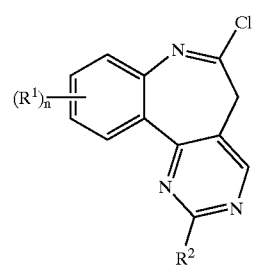

wherein the substituents $R^1$ and $R^2$ and n have the significances given above, and reacting this compound with

IV

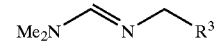

forming a compound of formula

V

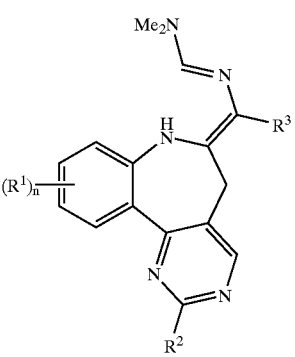

and cyclizing this compound with
MeCO$_2$H
forming a compound of formula

I

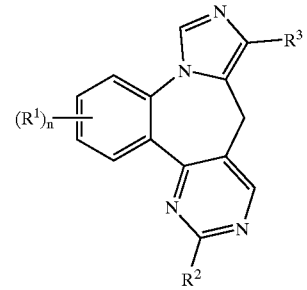

wherein $R^1$–$R^3$ and n have the significances given above, or reacting a compound of formula

III

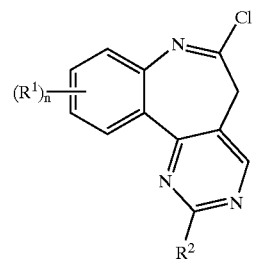

wherein the substituents $R^1$ and $R^2$ and n have the significances given in claim 1, with

forming a compound of formula I, or modifying one or more substituents $R^1$–$R^3$ within the definitions given above, and if desired, converting the compounds obtained into a pharmaceutically acceptable acid addition salt.

The salt formation is effected at room temperature in accordance with known methods that are familiar to any person skilled in the art. Not only salts with pharmaceutically acceptable inorganic acids, but also salts with pharmaceutically acceptable organic acids are possible. Hydrochlorides, hydrobromides, sulfates, nitrates, citrates, acetates, maleates, succinates, methanesulfonates, p-toluenesulfonates and the like are examples of such salts.

The following schemes 1, 1a, 2, 3, 4, 5 and 6 describe in more detail the process for preparation of compounds of formula I and/or their intermediates. The starting materials of formulas IV, VI, XVI, XX and XXVII are known compounds or maybe prepared according to methods known in the art.

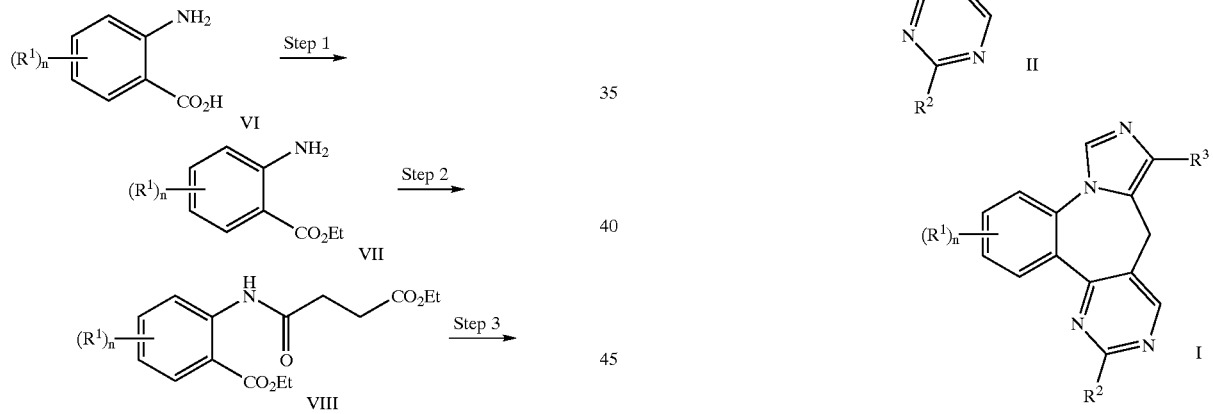

The substituents given in scheme 1 are described above.

Scheme 1a

Preparation of compounds of formula I in accordance with Step 7 in scheme 1:

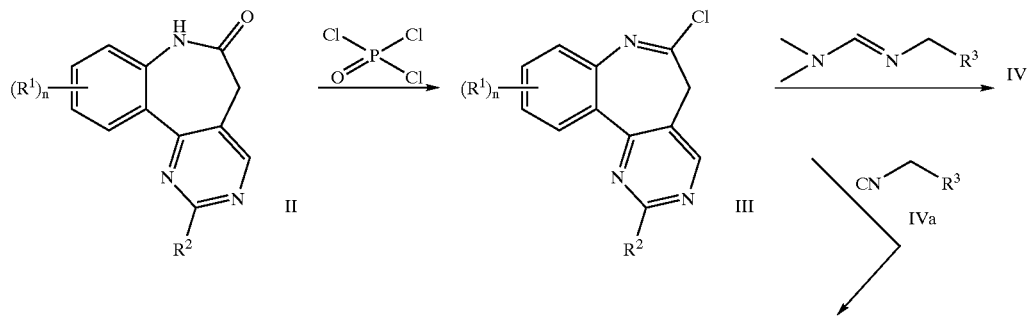

-continued

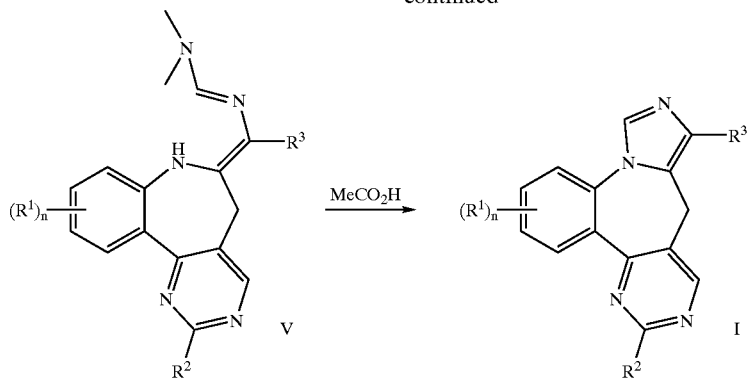

The substituents given in scheme 1a are described above.

Phosphoroxychloride may be replaced by the following equivalent compounds:

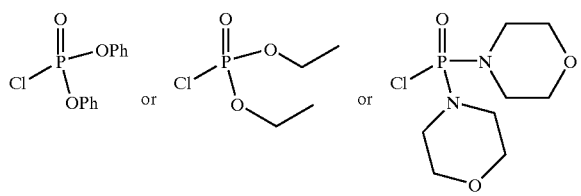

or methylsulfides in accordance with the following references:

J. Heterocycl. Chem., 1978, 15, 577–583
J. Org. Chem., 1976, 41, 2724–2727
J. Org. Chem., 1976, 41, 2720–2724 or
Synthesis, 1987, 162.

In accordance with schemes 1 and 1a a compound of formula I maybe prepared as follows: Starting from an appropriately substituted anthranilic acid (VI) the ester (VII) is prepared under standard conditions. Treatment of this product with an appropriate base and ethyl succinyl chloride to give the product (VIII) which is then reacted in an intramolecular Dieckmann cyclization to give the beta-keto ester products (IX). These are then de-ethoxy carboxylated under acidic or basic conditions to give the appropriately substituted benzazepinediones (X). Treatment of these products with dimethylformamide dimethoxy acetal provides the enaminone products (XI) which are then successively transformed to the 5,7-dihydro-6H-pyrimido[5,4-d][1]benzazepin-6-ones (II) by treatment with the appropriately substituted amidines (sometimes as salts) in the presence of sodium methoxide. The obtained compounds are then dissolved in phosphorus oxychloride and the solution heated and then evaporated. Then a solution of this product is added to a cold solution of either 1) ethyl isocyanoacetate and potassium tert-butoxide or 2) lithium diisopropylamide and (E)-(dimethylamino-methyleneamino)-acetic acid ester; and in a further step cyclized with addition of acetic acid followed by heating, The final products of formula I are purified in the conventional manner.

Scheme 2

Alternative method for the preparation of intermediates of formula VII:

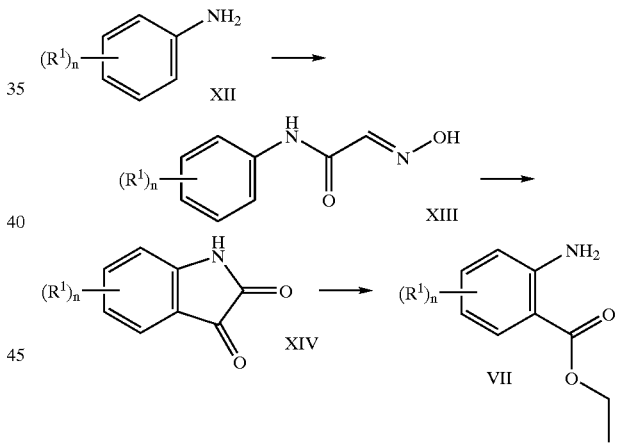

This process has also been described in J. Heterocyclic Chem., 1965, 2, 459.

Scheme 3

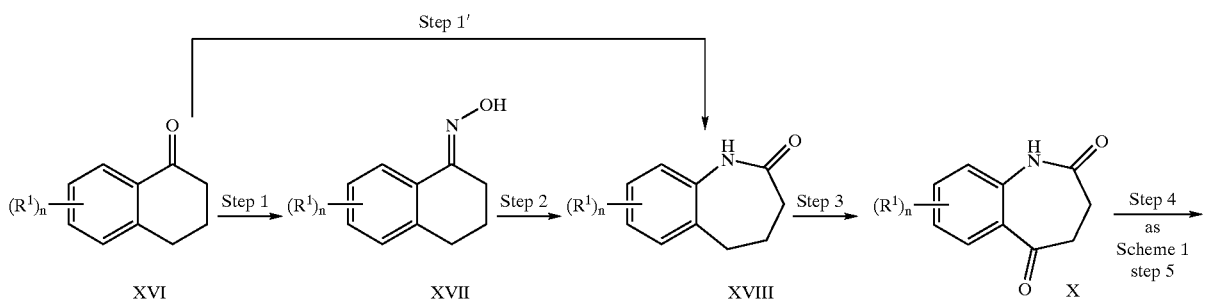

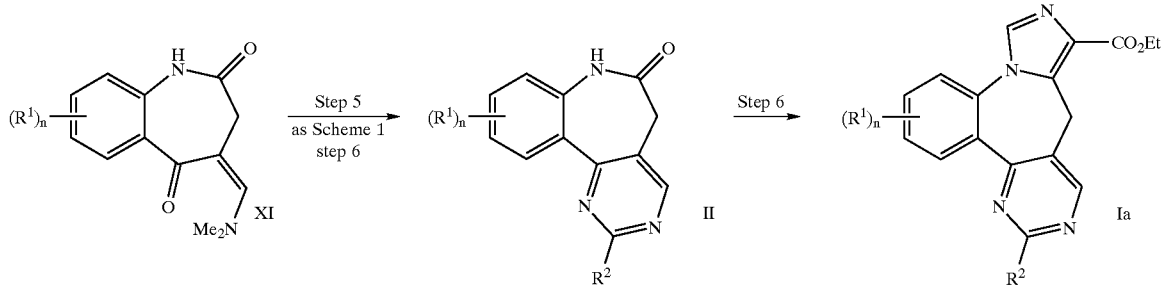

The substituents given in scheme 3 are described above.

A mixture of α-tetralone of formula XVI, hydroxylamine, sodium acetate and water/ethanol is treated under reflux for about 20 min and then cooled to 0° C. The obtained product is added to a solution of polyphosphoric acid at about 120° C. and heated. The lactam is then dissolved in BuOH and water, and then potassium permanganate is added followed by magnesium nitrate hexahydrate. This reaction is carried out at room temperature for about 48 h. A compound of formula Ia is then obtained followed by steps 5, 6 and 7 of scheme 1.

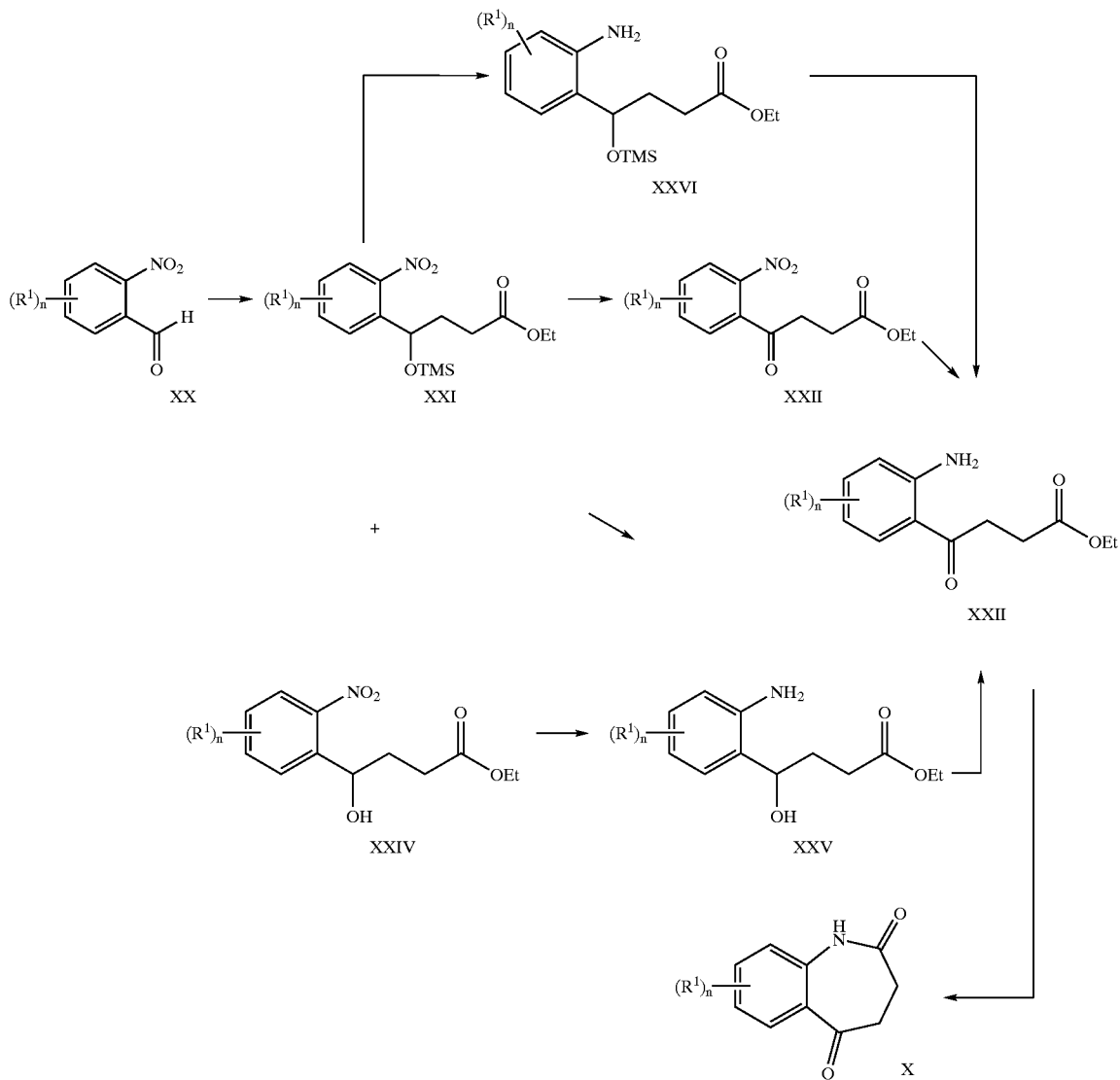

The substituents given in scheme 4 are described above.

The preparation of these intermediates is described in more detail in the working examples.

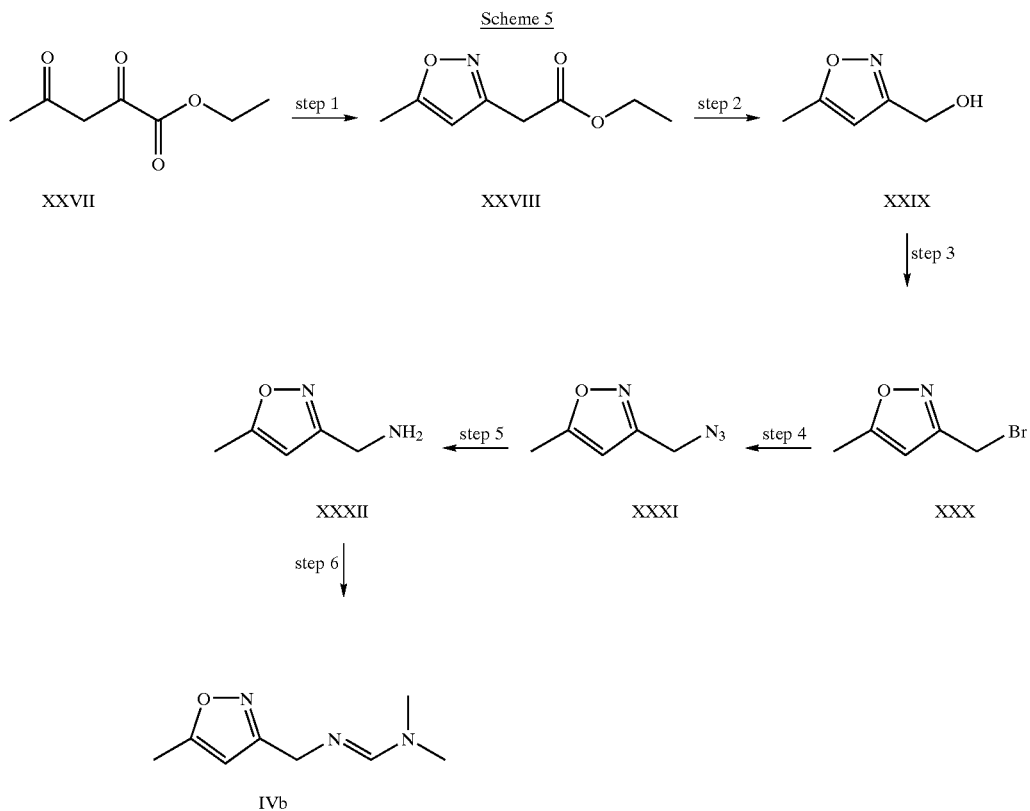

Scheme 5

In accordance with scheme 5, a compound of formula IVb has been prepared, which is used for the preparation of compounds of formula I, wherein R³ is an isoxazole group. This reaction is described in scheme 6.

In accordance with scheme 5, the following reaction steps are described in more detail:

Step 1: 5-Methyl-isoxazole-3-carboxylic Acid Ethyl Ester

To a solution of ethyl-2,4-dioxovalerate in ethanol is added hydroxylamine hydrochloride and sodium hydrogen carbonate. The reaction mixture is then heated under reflux for 1 hour. After cooling, the mixture is evaporated to leave a clear liquid that was distilled to leave the title compound.

Step 2: (5-Methyl-isoxazol-3-yl)-methanol

To a solution of 5-methyl-isoxazole-3-carboxylic acid ethyl ester in ethanol under argon at 0° C. is added portion wise NaBH₄ over 30 minutes. The reaction is allowed to warm up to room temperature (rt). After 3 h the reaction mixture is diluted with HCl and then after cooling to room temperature the mixture is washed with ether, the combined extracts are dried and evaporated.

Step 3: 3-Bromomethyl-5-methyl-isoxazole

To a solution of PBr₃ and pyridine in toluene is added at −10° C. a solution of hydroxymethyl-3-methyl-5-isoxazote in pyridine. The reaction mixture is then stirred at −10° C. for 1 h and stirred for about 14 h at rt. Then, the reaction mixture is diluted with water and extracted With ether. The combined extracts are then dried and evaporated. The residue is purified by chromatography.

Step 4: 3-Azidomethyl-5-methyl-isoxazole

To a solution of the 3-bromomethyl-5-methyl-isoxazole in acetone is added NaN₃ at rt. The reaction mixture is then stirred for about 48 h. Then, the reaction mixture is poured into water and extracted with EtOAc, dried and evaporated.

Step 5: (5-Methyl-isoxazol-3-yl)-methylamine

To a solution of the 3-azidomethyl-5-methyl-isoxazole in isopropanol at rt with vigorous stirring is added triethylamine, 1,3 propanedithiol and sodium borohydride. The mixture is then stirred at rt. After about 19 hours 0.5 eq more of NaBH₄ is added and stirred at rt for 7 hours more. Then the solvent is evaporated under vacuum and the residue is then dissolved in 10% aqueous citric acid and washed. The aqueous layer is basified with aqueous NaOH until pH 12, saturated with NaCl, and extracted with DCM. The combined DCM extracts are dried and concentrated.

Step 6: N,N-Dimethyl-N'-(5-methyl-isoxazol-3yl-methyl)-formamidine

A solution of the (5-methyl-isoxazol-3-yl)-methylamine in N,N-dimethylformamide dimethylacetal is heated under reflux for 3 h. After cooling to room temperature, the solvent is evaporated to leave the compound of formula IVa.

The compound of formula IVa may then be added to a compound of formula III according to schemes 1a and 6.

Scheme 6

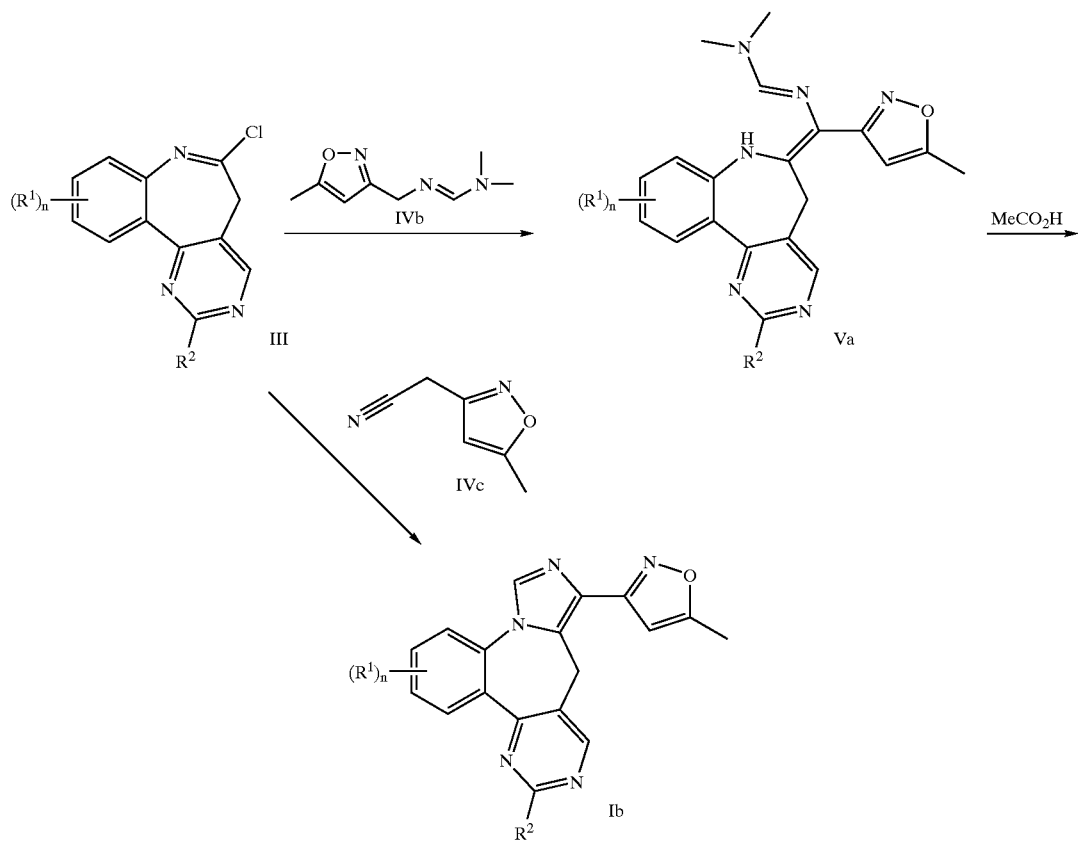

$R^1$, $R^2$ and n are described above.

As mentioned earlier, the compounds of formula I and their pharmaceutically acceptable salts possess valuable pharmacological properties. It has been found that the compounds of the present invention are ligands for GABA A receptors containing the α5 subunit and are therefore useful in the therapy where cognition enhancement is required.

The compounds of formula I were investigated in accordance with the test given hereinafter.

Membrane Preparation and Binding Assay

The affinity of compounds at GABA A receptor subtypes was measured by competition for [$^3$H]flumazenil ([$^3$H]Ro 15-1788) (85 Ci/mmol; Amersham) binding to SF9 cells expressing rat receptors of composition α1β3γ2, α2β3γ2, α3β3γ2 and α5β3γ2.

Cell pellets were suspended in Krebs-tris buffer (4.8 mM KCl, 1.2 mM CaCl$_2$, 1.2 mM MgCl$_2$, 120 mM NaCl, 15 mM Tris; pH 7.5; binding assay buffer), homogenized by polytron for ca. 15 sec on ice and centrifuged in UZ for 30 min at 4° C. (100000 g; rotor: TFT 4594=300,000 rpm). The cell pellets were re-suspended in Krebs-tris buffer and homogenized by polytron for ca. 15 sec on ice. Aliquots of 1 ml were prepared, protein was measured (Bradford method) and the resulting membrane aliquots were stored at −70° C.

Radioligand binding assays were carried out in a volume of 200 μL (96-well plates) which contained 100 μL of cells, [$^3$H]Ro 15-1788 at a concentration of 1 nM for (α1, α2, α3 subunits and 0.5 nM for α5 subunits and the test compound in the range of $10^{-10}$–$3\times10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above-described assay, and all were found to possess a Ki value for displacement of [$^3$H]Ro 15-1788 from α5 subunits of the rat GABA A receptor of 100 nM or less. In a preferred embodiment the compounds of the invention are binding selective for the α5 subunit relative to the α1, α2, and α1 subunit with an affinity of less then 15 nM.

The following specific data according to the test method described above for the especially preferred compounds of the present invention are presented in Table I below.

TABLE I

| Example No. | K$_i$ (nM) |
| --- | --- |
| 1 | 3.7 |
| 2 | 5.5 |
| 3 | 8.9 |
| 4 | 7.6 |
| 6 | 13.8 |
| 8 | 4.6 |
| 9 | 8.0 |

TABLE I-continued

| Example No. | $K_i$ (nM) |
| --- | --- |
| 10 | 11.2 |
| 11 | 7.8 |
| 22 | 12.5 |
| 29 | 3.8 |

The compounds of formula I as well as their pharmaceutically acceptable acid addition salts can be used as medicaments, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically acceptable acid addition salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used as such excipients e.g. vegetables dragées and hard gelatin capsules. Suitable excipients for soft excipients e.g. for vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain pharmaceutically acceptable preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. Unless stated to the contrary, all of the compounds listed as examples below were actually prepared and characterized as described. All temperatures are given in degrees Celsius.

EXAMPLE 1

9H-Imidazo[1,5-a]pyrimido[5,4-d][1]benzazepine-10-carboxylic Acid Ethyl Ester a) 2-Aminobenzoic Acid Ethyl Ester (Ethyl Anthranilate), Compound of Formula VII Prepared according to scheme 1, step 1, according to literature (Bamberger, Goldberger, J. Liebigs Ann. Chem., 1899, 362, 305).

Ethanol (500 mL) was cooled in ice and saturated with HCl gas. Then the 2-amino-benzoic acid (50 g) was added and the resulting mixture heated under reflux for 13 h. The hot solution was then poured onto ice-water 1.5 L and then the solution filtered neutralized with sodium hydrogen carbonate. The solution was then evaporated and then extracted with ether (3×200 mL) and the combined extracts dried and evaporated to leave a liquid which was distilled to give the product (49 g, 82%) as a clear liquid; m/z 165 (M).

b) 2-[(4-Ethoxy-1,4-dioxobutyl)amino)]-benzoic Acid Ethyl Ester (Compound of Formula VIII)

Prepared according to scheme 1, step 2.

To a stirred solution of ethyl anthranilate (50.0 g) in dry toluene (250 mL) at 0° C. was added calcium carbonate (60.6 g) followed by a solution of ethyl succinyl chloride (59.8 g) in dry toluene (400 mL) and the reaction mixture allowed to warm up to rt over 30 mins. The resulting mixture was then heated under reflux for 1 h and then the hot suspension was filtered. The solution was then evaporated to leave a white solid which was recrystallized from EtOH to give the product (82.1 g, 93%) as white crystals, m/z 293 (M).

c) 2,3-Dihydro-5-hydroxy-2-oxo-1H4-benzazepine-4-carboxylic Acid Ethyl Ester (Compound of Formula IX)

Prepared according to scheme 1, step 3.

To a suspension of KH in oil (20%, 39.6 g) was added toluene (60 mL) under argon.

To this suspension cooled to 10° C. was added the product of step 2 as a solution in toluene (90 mL), over 30 min (10–20° C.) followed by the addition of dry DMF (12 mL). After hydrogen evolution had stopped, the resulting mixture was heated at 70° C. for 2 h. After cooling, acetic acid (15 mL) was added with stirring followed by the addition of water (120 mL). The mixture was then filtered and the solid obtained was dried in the vacuum oven at 60° C. at 10 mbar, for 30 min. The solid (7.98 g) was then recrystallized from ethanol to give white needles (6.7 g, 84%), m/z 247 (M).

d) 3,4-Dihydro-1H-1-benzazepine-2,5-dione (Compound of Formula X)

Prepared according to scheme 1, step 4.

The product of step 3 (17.0 g,) was dissolved in DMSO (610 mL) and then water (30 mL) was added and the resulting mixture heated at 150° C. for 1 h. Then water (30 ml) was added and continued heating at 150° C. for 2 h. Then another aliquot of water (30 mL) was added and the mixture heated for another 2 h 20 min at 150° C. After cooling, the mixture was poured into water (600 mL) and the mixture was then extracted with DCM (3×250 mL), the combined extracts washed with water (250 mL), then dried and evaporated to leave an off-white orange solid. Recrystallization from EtOH afforded an off-white solid (6.0 g, 50%), m/z 175 (M).

e) 4[(Dimethylamino)methylene]-3,4-dihydro-1H-benzazepine-2,5-dione (Compound of Formula XI)

Prepared according to scheme 1, step 5.

A mixture of the product of step 4 (3.1 g) and N,N-dimethyformamide dimethylacetal (21.1 mL) was heated at 115–120° C. for 1 h. After cooling, the solid was filtered off and washed with ether, dried in the vacuum oven for 3 h at 50° C. at 1 mm Hg to leave a light orange solid (2.0 g, 58%), m/z (ISP) 231 (MH).

f) 5,7-Dihydro-6H-pyrimido[5,4-d][1]benzazepin-6-one (Compound of Formula II)

Prepared according to scheme 1, step 6.

To a mixture of the product from step 5 (4.6 g) in MeOH (160 mL) containing sodium methoxide (2.34 g) was added formamidine HCl (2.4 g) and the resulting mixture stirred at room temperature for 4 h. Then water (80 mL) was added and the resulting mixture was extracted with DCM (5×50 mL), and the combined extracts were dried over $Na_2SO4$. After evaporation, the residue was recrystallized from DCM: MeOH to leave off-white crystals (2.2 g, 52%), m/z 211 (M).

g) 9H-Imidazo [1,5-a]pyrimido[5,4-d][1]benzazepine-10-carboxylic Acid Ethyl Ester (Compound of Formula I)

Prepared according to scheme 1, step 7.

To a solution of the product from step 6 (2.2 g) in CHCl$_3$ (15 mL) was added N,N-dimethyl-p-toluidine (10. 3 mL) and phosphorus oxychloride (1.59 mL) and the resulting mixture heated under reflux for 1 h. After cooling, the mixture was poured into a solution of NaHCO$_3$ (8.2 g) in water (40 mL), and the resulting mixture was extracted with DCM (4×20 mL) and the combined extracts were then washed with water (40 mL), dried and evaporated to give the imino chloride. To a solution of ethyl isocyanoacetate (1.19 g) in dry DMF (20 mL) was added potassium tert-butoxide (1.26 g) and the resulting solution was added to a solution of the imino chloride (prepared as above) in dry DMF (5 mL) at −50° C. After 10 mins the reaction was allowed to warm up to room temperature (40 mins) and then acetic acid (0.5 mL) was added followed by ice-cold water (200 mL). The resulting mixture was extracted with DCM (4×40 mL) and the combined extracts washed with water (50 mL) and then dried over Na$_2$SO4 and evaporated. Chromatography of the residue on silica gel eluting with EtOAc: Hexane afforded the product (770 mg, 24%) as white crystals, mp 285–287° C., m/z 306 (M).

Alternative Reaction According to Scheme I

A mixture of the product from step 6 (1 mmol) and N,N-dimethyl-p-toluidine (2 mmol) were mixed in toluene (5 mL) and heated to 100° C. Then phosphorus oxychloride (1.1 mmol) was added dropwise and heating at 100° C. was continued for 1 h. The resulting mixture was then distilled under reduced pressure, and the residue was dissolved in THF (2 mL). To a solution of hexamethyldisilazane (3.3 mmol) in THF (2 mL) under Argon, at −75° C., was slowly added BuLi (1.6 M in hexanes, 3.3 mmol). After stirring for 1 h at −75° C., a solution of (E)-(dimethylaminomethyleneamino)-acetic acid ethyl ester (2.0 mmol) in THF (1.0 mL) was added and then continued stirring at −75° C. for 1 h. Then a solution of the appropriate imino chloride (prepared above) was added at −75° C., and then stirred for 1 h at −75° C. and then acetic acid (20 mmol) was added and the mixture allowed to warm up to 0° C., and then water (0.5 mL) was added and the mixture heated under reflux for 1 h. After cooling, the mixture was extracted with DCM (2×10 mL), and the combined extracts were washed with water (10 mL), and then evaporated. The residue was then purified by chromatography on silica gel or by preparative HPLC.

Examples 2–7 were prepared following Scheme 1 and Example 1.

EXAMPLE 2

6-Propyl-9H-imidazo[1,5-a]pyrimido[5,4-d][1]benzazepine-10-carboxylic Acid Ethyl Ester a) 5,7-Dihydro-2-propyl-6H-pyrimido[5,4-d][1]benzazepine-6-one Analogous to Scheme 1, from 4-[(dimethylamino)methylene]-3,4-dihydro-1H-benzazepine-2,5-dione and butyramidine hydrochloride. Yield: 84%.

White solid, m/z 253 (M).

b) 6-Propyl-9H-imidazo[1,5-a ]pyrimido[5,4-d][benzazepine-10-carboxylic Acid Ethyl Ester From 5,7-dihydro-2-propyl-6H-pyrimido[5,4-d][1]benzazepine-6-one according to scheme 1, step 7.

White solid, mp 180° C., m/z (ISP) 349 (MH).

EXAMPLE 3

6-(1-Methylethyl)-9H-imidazo [1,5-a]pyrimido[5,4-d][1]benzazepine-10-carboxylic Acid Ethyl Ester a) 5,7-Dihydro-2-(1-methylethyl)-6H-pyrimido[5,4-d][1]benzazepine-6-one Analogous to Scheme 1, from 4-[(dimethylamino)methylene]-3,4-dihydro-1H-benzazepine-2,5-dione and isobutyramidine hydrochloride. Yield: 87%.

White solid, m/z 253 (M).

b) 6-(1-Methylethyl)-9H-imidazo[1,5-a]pyrimido[5,4-d][1]benzazepine-10-carboxylic Acid Ethyl Ester From 5,7-dihydro-2-(1-methylethyl)-6H-pyrimido[5,4-d][1]benzazepine-6-one according to scheme 1, step 7.

White solid, mp 190° C., m/z (ISP) 349 (MH).

EXAMPLE 4

6-Cyclopropyl-9H-imidazo[1,5-a]pyrimido[5,4-d][1]benzazepine-10-carboxylic Acid Ethyl Ester a) 2-Cyclopropyl-5,7-dihydro-6H-pyrimido[5,4-d][1]benzazepine-6-one Analogous to Scheme 1 from 4-[(dimethylamino)methylene]-3,4-dihydro-1H-benzazepine-2,5-dione and cyclopropanecarboxamidine hydrochloride. Yield: 62%.

White solid, m/z (ISP) 252 (MH).

b) 6-Cyclopropyl-9H-imidazo[1,5-a]pyrimido[5,4-d][1]benzazepine-10-carboxylic Acid Ethyl Ester From 2-cyclopropyl-5,7-dihydro-6H-pyrimido[5,4-d][1]benzazepine-6-one according to scheme 1, step 7.

White solid, mp 110° C., m/z (ISP) 347 (MH).

EXAMPLE 5

6-(1,1-Dimethylethyl)-9H-imidazo[1,5-a]pyrimido[5,4-d][1]benzazepine-10-carboxylic Acid Ethyl Ester a) 2-(1,1-Dimethylethyl)-5,7-dihydro-6H-pyrimido[5,4-d][1]benzazepine-6-one Analogous to Scheme 1, from 4-[(dimethylamino)methylene]-3,4-dihydro-1H-benzazepine-2,5-dione and 2,2-dimethylpropionamidine hydrochloride. Yield: 90%.

White solid, m/z 267(M).

b) 6-(1,1-Dimethylethyl)-9H-imidazo[1,5-a]pyrimido[5,4-d][1]benzazepine-10-carboxylic Acid Ethyl Ester From 2-(1,1-dimethylethyl)-5,7-dihydro-6H-pyrimido[5,4-d][1]benzazepine-6-one according to scheme 1, step 7.

White solid, mp 250° C., m/z (ISP) 363 (MH).

EXAMPLE 6

6-[(4-Methoxyphenyl)Methyl]-9H-imidazo[1,5-a]pyrimido[5,4-d][1]benzazepine-10-carboxylic Acid Ethyl Ester a) 5,7-Dihydro-2-[(4-Methoxyphenyl)methyl]-6H-pyrimido[5,4-d][1]benzazepine-6-one Analogous to Scheme 1, from 4-[(dimethylamino)methylene]-3,4-dihydro-1H-benzazepine-2,5-dione and 2-(4-methoxyphenyl)-acetamidine hydrochloride. Yield: 31%. White solid, m/z (ISP) 332 (MH).

b) 6-[(4-Methoxyphenyl)methyl]-9H-imidazo[1,5-a]pyrimido[5,4-d][1]benzazepine-10-carboxylic Acid Ethyl Ester From 5,7-dihydro-2-[(4-methoxyphenyl)methyl]-6H-pyrimido[5,4-d][1]benzazepine-6-one according to scheme 1, step 7.

White solid, mp 200° C., m/z (ISP) 427 (M).

EXAMPLE 7

6-(1H-Indol-3-ylmethyl)-9H-imidazo[1,5-a]
pyrimido[5,4-d][1]benzazepine-10-carboxylic Acid
Ethyl Ester a) 5,7-Dihydro-2-(1H-indol-3-ylmethyl)-6H-pyrimido[5,4-d][1]benzazepine-6-one Analogous to Scheme 1, from 4-[(dimethylamino)methylene]-3,4-dihydro-1H-benzazepine-2,5-dione and 2-(1H-indol-3-yl)-acetamidine. Yield: 80%.
White solid, m/z 340 (M).

c) 6-(1H-Indol-3-yl-methyl)-9H-imidazo[1,5-a]pyrimido[5,4]-d[1]benzazepine-10-carboxylic Acid Ethyl Ester From 5,7-dihydro-2-(1H-indol-3-ylmethyl)-6H-pyrimido[5,4-d][1]benzazepine-6-one according to scheme 1, step 7.
White solid, mp 120° C., m/z (ISP) 436 (M).

EXAMPLE 8

3-Fluoro-6-methyl-9H-imidazo[1,5-a]pyrimido[5,4-d][1]benzazepine-10-carboxylic Acid Ethyl Ester a) 2-Amino-5-fluoro-benzoic Acid Ethyl Ester (Compound of Formula VII)

Prepared in accordance with schemes 1 or 2.
light yellow liquid, bp 68–70° C. at 0.4 mbar.

b) 2-[(4-Ethoxy-1,4-dioxobutyl)Amino)]-5-fluoro-benzoic Acid Ethyl Ester (Compound of Formula VIII)

Prepared from 2-amino-5-fluoro-benzoic acid ethyl ester in accordance with scheme 1, step 2. Yield: 100%.
White solid, m/z 311 (M).

c) 7-Fluoro-2,3-dihydro-5-hydroxy-2-oxo-1H-benzazepine-4-carboxylic Acid Ethyl Ester (Compound of Formula IX)

Prepared from 2-[(4-ethoxy-1,4-dioxobutyl)amino)]-5-fluoro-benzoic acid ethyl ester in accordance with scheme 1, step 3. Yield: 69%.
White solid, m/z 265 (M).

d) 7-Fluoro-3,4-dihydro-1H-1-benzazepine-2,5-dione (Compound of Formula X)

Prepared from 7-fluoro-2,3-dihydro-5-hydroxy-2-oxo-1H-benzazepine-4-carboxylic acid ethyl ester in accordance with scheme 1, step 4. Yield: 67%.
White solid, m/z 193 (M).

e) 4-(Dimethylamino)Methylenel-7-fluoro-3,4-dihydro-1H-benzazepine-2,5-dione (Compound of Formula XI)

Prepared from 7-fluoro-3,4-dihydro-1H-1-benzazepine-2,5-dione in accordance with scheme 1, step 5. Yield: 75%.
Light orange solid, m/z 248 (M).

f) 10-Fluoro-5,7-dihydro-2-methyl-6H-pyrimido[5,4-d][1]benzazepin-6-one (Compound of Formula II)

Analogous to Scheme 1, from 4-[(dimethylamino)methylene]-7-fluoro-3,4-dihydro-1H-benzazepine-2,5-dione and acetamidine hydrochloride. Yield: 50%.
White solid, m/z (ISP) 244 (MH).

g) 3-Fluoro-6-methyl-9H-imidazo[1,5-a]pyrimido[5,4-d][1]benzazepine-10-carboxylic Acid Ethyl Ester (Compound of Formula I)

Prepared from 10-fluoro-5,7-dihydro-2-methyl-6H-pyrimido[5,4-d][1]benzazepin-6-one in accordance with scheme 1, step 7.
White solid, mp 230° C., m/z 338 (M).

EXAMPLE 9

3-Fluoro-6-propyl-9H-imidazo[1,5-a]pyrimido[5,4-d][1]benzazepine-10-carboxylic Acid Ethyl Ester a) 10-Fluoro-5,7-dihydro-2-propyl-6H-pyrimido[5,4-d][1]benzazepin-6-one Analogous to Scheme 1, from 4-[(dimethylamino)methylene]-7-fluoro-3,4-dihydro-1H-benzazepine-2,5-dione and butyramidine hydrochloride. Yield: 50%.
White solid, m/z (ISP) 272 (MH).

b) 3-Fluoro-6-propyl-9H-imidazo]1,5-a]pyrimido[5,4-d][1]benzazepine-10-carboxylic Acid Ethyl Ester From 10-fluoro-5,7-dihydro-2-propyl-6H-pyrimido [5,4-d][1]benzazepin-6-one according to scheme 1, step 7.
White solid, mp 200° C., m/z (ISP) 367 (MH).

EXAMPLE 10

3-Fluoro-6-(1-methylethyl)-9H-imidazo[1,5-a]
pyrimido[5,4-d][1]benzazepine-10-carboxylic Acid
Ethyl Ester a) 10-Fluoro-5,7-dihydro-2-(1-methylethyl)-6H-pyrimido[5,4-d][1]benzazepin-6-one Analogous to Scheme 1, from 4-[(dimethylamino)methylene]-7-fluoro-3,4-dihydro-1H-benzazepine-2,5-dione and isobutyramidine hydrochloride. Yield: 60%.
White solid, m/z (ISP) 272 (MH).

b) 10-Fluoro-6-(1-methylethyl)-9H-imidazo[1,5-a]pyrimido [5.4-d][1]benzazepine-10-carboxylic Acid Ethyl Ester From 10-fluoro-5,7-dihydro-2-(1-methylethyl)-6H-pyrimido[5,4-d][1]benzazepin-6-one according to scheme 1, step 7.
White solid, mp 185° C., m/z (ISP) 367 (MH).

EXAMPLE 11

6-Cyclopropyl-3-fluoro-9H-imidazo[1,5-a]pyrimido
[5,4-d][1]benzazepine-10-carboxylic Acid Ethyl
Ester a) 2-Cyclopropyl-10-fluoro-5,7-dihydro-6H-pyrimido[5,4-d][1]benzazepin-6-one Analogous to Scheme 1, from 4-[(dimethylamino)methylene]-7-fluoro-3,4-dihydro-1H-benzazepine-2,5-dione and cyclopropanecarboxamidine hydrochloride. Yield: 88%.
White solid, m/z (ISP) 270 (MH).

b) 6-Cyclopropyl-3-fluoro-9H-imidazo[5-a]pyrimido[5,4-d][1]benzazepine-10-carboxylic Acid Ethyl Ester From 2-cyclopropyl-10-fluoro-5,7-dihydro-6H-pyrimido [5,4-d][1]benzazepin-6-one according to scheme 1, step 7.
White solid, mp 220° C., m/z (ISP) 365 (MH).

EXAMPLE 12

3-Fluoro-6-(1,1-dimethylethyl)-9H-imidazo[1,5-a]
pyrimido[5,4-d][1]benzazepine-10-carboxylic Acid
Ethyl Ester a) 2-(1,1-Dimethylethyl)-10-fluoro-5,7-dihydro-6H-pyrimido[5.4-d][1]benzazepin-6-one Analogous to Scheme 1, from 4-[(dimethylamino)methylene]-7-fluoro-3,4-dihydro-1H-benzazepine-2,5-dione and 2,2-dimethylpropionamidine hydrochloride. Yield: 54%.
White solid, m/z (ISP) 286 (MH).

b) 3-Fluoro-6-(1,1-dimethylethyl)-9H-imidazo[1,5-a]pyrimido[5,4-d][1]benzazepine-10-carboxylic Acid Ethyl Ester From 2-(1,1-dimethylethyl)-10-fluoro-5,7-dihydro-6H-pyrimido[5,4-d][1]benzazepin-6-one according to scheme 1, step 7.
White solid, mp 233° C., m/z (ISP) 381 (MH).

EXAMPLE 13

3-Fluoro-6-[(4-methoxyphenyl) Methyl]-9H-
imidazo [1,5-a]pyrimido [5,4-d][1]benzazepine-10-
carboxylic Acid Ethyl Ester a) 10-Fluoro-5,7-dihydro-2-[(4-methoxyphenyl)Methyl]-6H-pyrimido[5,4-d][1]benzazepin-6-one Analogous to Scheme 1, from 4-[(dimethylamino)methylene]-7-fluoro-3,4-dihydro-1H-benzazepine-2,5-dione and 2-(4-methoxyphenyl)-acetamidine hydrochloride. Yield: 89%. White solid, m/z (ISP) 350 (MH).

b) 3-Fluoro-6-[(4-methoxyphenyl)methyl]-9H-imidazo[1,5-a]pyrimido[5,4-d][1]benzazepine-10-carboxylic Acid Ethyl Ester From 10-fluoro-5,7-dihydro-2-[(4-methoxyphenyl)methyl]-6H-pyrimido[5,4-d][1]benzazepin-6-one according to scheme 1, step 7.
White solid, mp 185° C., m/z (ISP) 445 (MH).

EXAMPLE 14

3-Fluoro-6-(1H-indol-3-ylmethyl)-9H-imidazo[1,5-a]pyrimido[5,4-d][1]benzazepine-10-carboxylic Acid Ethyl Ester a) 10-Fluoro-5,7-dihydro-2-(1H-indol-3-ylmethyl)-6H-pyrimido[5,4-d][1]benzazepin-6-one Analogous to Scheme 1, from 4-[(dimethylamino)methylene]-7-fluoro-3,4-dihydro-1H-benzazepine-2,5-dione and 2-(1H-indol-3-yl)-acetamidine. Yield: 87%.
White solid, m/z (ISP) 359 (MH).

b) 3-Fluoro-6-(1H-indol-3-yl methyl)-9H-imidazo[1,5-a]pyrimido[5,4-d][1]benzazepine-10-carboxylic Acid Ethyl Ester From 10-fluoro-5,7-dihydro-2-(1H-indol-3-ylmethyl)-6H-pyrimido[5,4-d][1]benzazepin-6-one according to scheme 1, step 7.
White solid, mp 230° C., m/z (ISP) 454 (MH).

EXAMPLE 15

3-Chloro-6-methyl-9H-imidazo[1,5-a]pyrimido[5,4-d][1-benzazepine-10-carboxylic Acid Ethyl Ester a) 2-Amino-5-chloro-benzoic Acid Ethyl Ester (Compound of Formula VII)

Prepared from ethyl anthranilate and sodium hypochlorite (according to M. Okabe and R-C Sun, Tetrahedron, 1995, 51, 1861) to give an off-white solid, mp 80° C., m/z 199.

b) 5-Chloro-2-[(4-ethox-1,4-dioxobutyl)Amino)]-benzoic Acid Ethyl Ester (Compound of Formula VIII)

From 2-amino-5-chloro-benzoic acid ethyl ester according to scheme 1 step 2.
Yield: 100%. White solid, m/z 327 (M).

c) 7-Chloro-2,3-dihydro-5-hydroxy-2-oxo-1H-benzazepine-4-carboxylic Acid Ethyl Ester (Compound of Formula IX)

From 5-chloro-2-[(4-ethoxy-1,4-dioxobutyl)amino)]-benzoic acid ethyl ester according to scheme 1, step 3. Yield: 81%.
White solid, m/z 281 (M).

d) 7-Chloro-3,4-dihydro-1H-1-benzazepine-2,5-dione (Compound of Formula X)

From 7-chloro-2,3-dihydro-5-hydroxy-2-oxo-1H-benzazepine-4-carboxylic acid ethyl ester according to scheme 1, step 4. Yield: 48%.
White solid, m/z 209 (M).

f) 7-Chloro-4-[(dimethylamino)Methylene]-3,4-dihydro-1H-benzazepine-2,5-dione (Compound of Formula XI)

From 7-chloro-3,4-dihydro-1H-1-benzazepine-2,5-dione according to scheme 1, step 5.
Yield: 79%. Light orange solid, m/z 264 (M).

f) 10-Chloro-5,7-dihydro-2-methyl-6H-pyrimido[5,4-d][1]benzazepin-6-one (Compound of Formula II)

Analogous to Scheme 1, from 7-chloro-4-[(dimethylamino)methylene]-3,4-dihydro-1H-benzazepine-2,5-dione and acetamidine hydrochloride. Yield: 58%.
White solid, m/z 259 (M).

g) 3-Chloro-6-methyl-9H-imidazo[1,5-a]pyrimido[5,4-d][1]benzazepine-10-carboxylic Acid Ethyl Ester One (Compound of Formula I)

From 10-chloro-5,7-dihydro-2-methyl-6H-pyrimido[5,4-d][1]benzazepin-6-one according to scheme 1, step 7.
White solid, mp 202–204° C., m/z (ISP) 355 (MH).

EXAMPLE 16

3-Chloro-6-(1-methylethyl)-9H-imidazo[1,5-a]pyrimido[5,4-d][1]benzazepine-10-carboxylic Acid Ethyl Ester a) 10-Chloro-5,7-dihydro-2-(1-methylethyl)-6H-pyrimido-5,4-d][1]benzazepin-6-one Analogous to Scheme 1, from 7-chloro-4-[(dimethylamino)methylene]-3,4-dihydro-1H-benzazepine-2,5-dione and isobutyramidine hydrochloride. Yield: 87%.
White solid, m/z (ISP) 288 (MH).

b) 3-Chloro-6-(1-methylethyl)-9H-imidazo [1,5-a]pyrimido[5,4-d][1]benzazepine-10-carboxylic Acid From 10-chloro-5,7-dihydro-2-(1-methylethyl)-6H-pyrimido[5,4-d][1]benzazepin-6-one according to scheme 1 step 7.
White solid, mp 192° C., m/z (ISP) 383 (MH).

EXAMPLE 17

3-Chloro-6-cyclopropyl-9H-imidazo[1,5-a]pyrimido[5,4-d][1]benzazepine-10-carboxylic Acid Ethyl Ester a) 10-Chloro-2-cyclopropyl-5,7-dihydro-6H-pyrimido[5,4-d][1]benzazepin-6-one Analogous to Scheme 1, from 7-chloro-4-[(dimethylamino)methylene]-3,4-dihydro-1H-benzazepine-2,5-dione and cyclopropancarboxamidine hydrochloride. Yield: 83%.
White solid, m/z (ISP) 28 (MH).

b) 3-Chloro-6-cyclopropyl-9H-imidazo[5-a]pyrimido[5,4-d][1]benzazepine-10-carboxylic Acid Ethyl Ester From 10-chloro-2-cyclopropyl-5,7-dihydro-6H-pyrimido[5,4-d][1]benzazepin-6-one according to scheme 1, step 7.
White solid, mp 230° C., m/z (ISP) 381 (MH).

EXAMPLE 18

3-Chloro-6-(1,1-dimethylethyl)-9H-imidazo[1,5-a]pyrimido[5,4-d][1]benzazepine-10-carboxylic Acid Ethyl Ester a) 10-Chloro-2-(1,1-dimethylethyl)-5,7-dihydro-6H-pyrimido[5,4-d][1]benzazepin-6-one Analogous to Scheme 1, from 7-chloro-4-[(dimethylamino)methylene]-3,4-dihydro-1H-benzazepine-2,5-dione and 2,2-dimethylpropionamidine hydrochloride. Yield: 88%. Off-white solid, m/z (ISP) 302 (MH)

b) 3-Chloro-6-(1,1-dimethylethyl)-9H-imidazo[1,5-a]pyrimido[5,4-d][1]benzazepine-10-carboxylic Acid Ethyl Ester From 10-chloro-2-(1,1-dimethylethyl)-5,7-dihydro-6H-pyrimido[5,4-d][1]benzazepin-6-one according to scheme 1, step 7.
White solid, mp 180° C. m/z (ISP) 397 (MH).

EXAMPLE 19

3-Chloro-6-[(4-methoxyphenyl)Methyl)-9H-imidazo[1,5-a]pyrimido[5,4-d][1]benzazepine-10-carboxylic Acid Ethyl Ester a) 10-Chloro-5,7-dihydro-2-[(4-methoxyphenyl)Methyl]-6H-pyrimido[5,4-d][1]benzazepin-6-one Analogous to Scheme 1, from 7-chloro-4-[(dimethylamino)methylene]-3,4-dihydro-1H-benzazepine-2,5-dione and 2-(4-methoxyphenyl)-acetamidine hydrochloride. Yield: 87%. White solid, m/z (ISP) 366 (MH).

b) 3-Chloro-6-[(4-methoxyphenyl)Methyl)-9H-imidazo-1, 5-a]pyrimido[5,4-d][1]benzazepine-10-carboxylic Acid Ethyl Ester From 10-chloro-5,7-dihydro-2-[(4-methoxyphenyl) methyl]-6H-pyrimido[5,4-d][1]benzazepin-6-one according to scheme 1, step 7.
White solid, mp 192° C., m/z (ISP) 461 (MH).

EXAMPLE 20

3-Chloro-6-(1H-indol-3-ylmethyl)-9H-imidazo[1,5-a]pyrimido[5,4-d][1]benzazepine-10-carboxylic Acid Ethyl Ester a) 10-Chloro-5,7-dihydro-2-(1H-indol-3-ylmethyl)-6H-pyrimido[5,4-d][1]benzazepin-6-one Analogous to Scheme 1, from 7-chloro-4-[(dimethylamino)methylene]-3,4-dihydro-1H-benzazepine-2,5-dione and 2-(1H-indol-3-yl)-acetamidine. Yield: 46%.
White solid, m/z 374 (M).

b) 3-Chloro-6-(1H-indol-3-yl-methyl)-9H-imidazo[1,5-a]pyrimido[5,4-d][1]benzazepine-10-carboxylic Acid Ethyl Ester From 10-chloro-5,7-dihydro-2-(1H-indol-3-ylmethyl)-6H-pyrimido[5,4-d][1]benzazepin-6-one according, to scheme 1, step 7.
White solid, mp 120° C., m/z (ISP) 470 (MH).

EXAMPLE 21

3-Bromo-9H-imidazo[1,5-a]pyrimido[5,4-d][1]benzazepine-10-carboxylic Acid Ethyl Ester a) 2-Amino-5-bromo-benzoic Acid Ethyl Ester (Compound of Formula VII)

As in scheme 1 step 1, from 2-amino-5-bromobenzoic acid, ethanol and HCl gas and heating under reflux for 16 h to afford an off-white solid, mp 83° C.

b) 5-Bromo-2-[(4-ethoxy-1,4-dioxobutyl)Amino)]-benzoic Acid Ethyl Ester (Compound of Formula VIII)

From 2-amino-5-bromo-benzoic acid ethyl ester according to scheme 1, step 2. Yield: 79%. White solid, m/z (ISP) 371/373 (MH).

c) 7-Bromo-2,3-dihydro-5-hydroxy-2-oxo-1H-benzazepine-4-carboxylic Acid Ethyl Ester (Compound of Formula IX)

From 5-bromo-2-[(4-ethoxy-1,4-dioxobutyl)amino)]-benzoic acid ethyl ester according to scheme 1, step 3. Yield: 71%.
White solid, m/z (ISP) 325/327 (MH).

d) 7-Bromo-3,4-dihydro-1H-1-benzazepine-2,5-dione (Compound of Formula X)

From 7-bromo-2,3-dihydro-5-hydroxy-2-oxo-1H-benzazepine-4-carboxylic acid ethyl ester according to scheme 1 step 4. Yield: 65%.
White solid, m/z (ISP) 253/255 (MH)

e) 7-Bromo-4-[(dimethylamino)Methylene]-3,4-dihydro-1H-benzazepine-2,5-dione (Compound of Formula XI)

From 7-bromo-3,4-dihydro-1H-1-benzazepine-2,5-dione according to scheme 1, step 5. Yield: 90%. Light orange solid, m/z (ISP) 309/311 (MH).

f) 10-Bromo-5,7-dihydro-6H-pyrimido[5,4-d][1]benzazepin-6-one (Compound of Formula II)

Analogous to Scheme 1, from 7-bromo-4-[(dimethylamino)methylene]-3,4-dihydro-1H-benzazepine-2,5-dione and formamidine acetate. Yield: 83%.
white solid, m/z (ISP) 2(89/291 (MH).

g) 3-Bromo-9H-imidazo[1,5-a]pyrimido[5,4-d][1]benzazepine-10-carboxylic Acid Ethyl Ester From 10-bromo-5,7-dihydro-6H-pyrimido[5,4-d][1]benzazepin-6-one according to scheme 1, step 7.
White solid, mp 210° C., m/z (ISP) 385/387 (MH)

EXAMPLE 22

3-Bromo-6-methyl-9H-imidazo[1,5-a]pyrimido[5,4-d][1]benzazepine-10-carboxylic Acid Ethyl Ester a) 10-Bromo-5,7-dihydro-2-methyl-6H-pyrimido[5,4-d][1]benzazepin-6-one Analogous to Scheme 1, from 7-bromo-4-[dimethylamino)methylene]-3,4-dihydro-1H-benzazepine-2,5-dione and acetamidine hydrochloride. Yield: 87%.
White solid, m/z (ISP) 303/305 (MH)

b) 3-Bromo-6-methyl-9H-imidazo[1,5-a]1-pyrimido[5,4-d][1]benzazepine-10-carboxylic Acid Ethyl Ester From 1-bromo-5,7-dihydro-2-methyl-6H-pyrimido[5,4-d][1]benzazepin-6-one according to scheme 1, step 7.
White solid, mp 130° C., m/z (ISP) 399/401 (MH)

EXAMPLE 23

3-Bromo-6-cyclopropyl-9H-imidazo[1,5-a]pyrimido[5,4-d][1]benzazepine-10-carboxylic Acid Ethyl Ester a) 10-Bromo-5,7-dihydro-2-cyclopropyl-(6H-pyrimido[5,4-d][1]benzazepin-6-one Analogous to Scheme 1, from 7-bromo-4-[(dimethylamino)methylene]-3,4-dihydro-1H-benzazepine-2,5-dione and cyclopropanecarboxamidine hydrochloride. Yield: 99%.
White solid, m/z (ISP) 330/332 (MH).

b) 3-Bromo-6-cyclopropyl-9H-imidazo[1,5-a]pyrimido[5,4-d][1]benzazepine-10-carboxylic Acid Ethyl Ester From 10-bromo-5,7-dihydro-2-cyclopropyl-6H-pyrimido[5,4-d][1]benzazepin-6-one according to scheme 1, step 7.
White solid, mp 230° C., m/z (ISP) 425/427 (MH).

EXAMPLE 24

3-Bromo-6-[(4-methoxyphenyl)Methyl]-9H-imidazo[1,5-a]pyrimido[5,4-d][1]benzazepine-10-carboxylic Acid Ethyl Ester a) 10-Bromo-5,7-dihydro-2-[(4-methoxyphenyl)methyl]-6H-pyrimido[5,4-d][1]benzazepin-6-one Analogous to Scheme 1, from 7-bromo-4-[(dimethylamino)methylene]-3,4-dihydro-1H-benzazepine-2,5-dione and 2-(4-methoxyphenyl)-acetamidine hydrochloride. Yield: 99%. White solid, m/z (ISP) 410/412 (MH).

b) 3-Bromo-6-[(4-methoxyphenyl)Methyl]-9H-imidazo[1, 5-a]pyrimido[5,4-d][1]benzazepine-10-carboxylic Acid Ethyl Ester From 10-bromo-5,7-dihydro-2-[(4-methoxyphenyl) methyl]-6H-pyrimido[5,4-d][1]benzazepin-6-one according to scheme 1, step 7.
White solid, mp 180° C., m/z (ISP) 505/507 (MH).

EXAMPLE 25

3,6-Dimethyl-9H-imidazo[1,5-a]pyrimido[5,4-d][1]benzazepine-10-carboxylic Acid Ethyl Ester a) 2-Amino-5-methyl-benzoic Acid Ethyl Ester (Compound of Formula VII)

As in scheme 1 step 1 (according to S. P. Acharya and J. B. Hynes, J. Heterocyclic Chem., 1975, 12, 1283) from 2-amino-5-methylbenzoic acid, ethanol and HCl gas to afford the product. Yield: 80%.
White solid, m/z (ISP) 178 (M-H)

b) 2-[(4-Ethoxy-1,4-dioxobutyl)Amino)]-5-methyl-benzoic Acid Ethyl Ester (Compound of Formula VIII)

From 2-amino-5-methyl-benzoic acid ethyl ester according to scheme 1 step 2. Yield: 87%. White solid, m/z (ISP) 308 (MH).

c) 2,3-Dihydro-5-hydroxy-7-methyl-2-oxo-1H-benzazepine-4-carboxylic Acid Ethyl Ester (Compound of Formula IX)

From 2-[(4-ethoxy-1,4-dioxobutyl)amino)]-5-methyl-benzoic acid ethyl ester according to scheme 1 step 3. Yield: 41%.
White solid, m/z (ISP) 262 (MH).

d) 3,4-Dihydro-7-methyl-1H-1-benzazepine-2,5-dione (Compound of Formula X)

From 2,3-dihydro-5-hydroxy-7-methyl-2-oxo-1H-benzazepine-4-carboxylic acid ethyl ester according to scheme 1, step 4. Yield: 98%.
White solid, m/z (ISP) 190 (MH).

e) 4-[(Dimethylamino)Methylene]-3,4-dihydro-7-methyl-1H-benzazepine-2,5-dione (Compound of Formula XI)

From 3,4-dihydro-7-methyl-1H-1-benzazepine-2,5-dione according to scheme 1 step 5.
Yield: 74%. Light brown solid, m/z (ISP) 245 (MH).

f) 5,7-Dihydro-2,10-dimethyl-6H-pyrimido[5,4-d][1]benzazepin-6-one (Compound of Formula II)

Analogous to Scheme 1, from 4-[(dimethylamino) methylene]-3,4-dihydro-7-methyl-1H-benzazepine-2,5-dione and acetamidine hydrochloride. Yield: 98%.
White solid, m/z (ISP) 240 (MH).

g) 3,6-Dimethyl-9H-imidazo[1,5-a]pyrimido[5,4-d][1]benzazepine-10-carboxylic Acid Ethyl Ester (Compound of Formula I)

From 5,7-dihydro-2,10-dimethyl-6H-pyrimido[5,4-d][1]benzazepin-6-one according to scheme 1, step 7.
White solid, mp 200° C., m/z (ISP) 335 (MH).

EXAMPLE 26

3-Methyl-6-propyl-9H-imidazo[1,5-a]pyrimido[5,4-d][1]benzazepine-10-carboxylic Acid Ethyl Ester a) 5,7-Dihydro-10-methyl-2-propyl-6H-pyrimido[5,4-d][1]benzazepin-6-one Analogous to Scheme 1, from 4-[(dimethylamino) methylene]-3,4-dihydro-7-methyl-1H-benzazepine-2,5-dione and butyramidine hydrochloride. Yield: 90%.
White solid, m/z (ISP) 268 (MH).

b) 3-Methyl-6-propyl-9H-imidazo[1,5-a]pyrimido[5,4-d][1]benzazepine-10-carboxylic Acid Ethyl Ester From 5,7-dihydro-10-methyl-2-propyl-6H-pyrimido[5,4-d][1]benzazepin-6-one according to scheme 1, step 7.
White solid, mp 250° C., m/z (ISP) 363 (MH).

EXAMPLE 27

3-Methyl-6-(1-methylethyl)-9H-imidazo[1,5-a] pyrimido[5,4-d][1]benzazepine-10-carboxylic Acid Ethyl Ester a) 5,7-Dihydro-10-methyl-2-(1-methylethyl)-6H-pyrimido[5,4-d][1]benzazepin-6-one Analogous to Scheme 1 from 4-[(dimethylamino) methylene]-3,4-dihydro-7-methyl-1H-benzazepine-2,5-dione and isobutyramidine hydrochloride. Yield: 91%.
White solid, m/z (ISP) 268 (MH).

b) 3-Methyl-6-(1-methylethyl)-9H-imidazo[1,5-a]pyrimido[5,4-d][1]benzazepine-10-carboxylic Acid Ethyl Ester From 5,7-dihydro-10-methyl-2-(1-methylethyl)-6H-pyrimido[5,4-d][1]benzazepin-6-one according to scheme 1 step 7.
White solid, mp 190 m/z (ISP) 363 (MH).

EXAMPLE 28

6-Cyclopropyl-3-methyl-9H-imidazo[1,5-a]pyrimido [5,4-d][1]benzazepine-10-carboxylic Acid Ethyl Ester a) 2-Cyclopropyl-5,7-dihydro-10-methyl-6H-pyrimido[5,4-d][1]benzazepin-6-one Analogous to Scheme 1, from 4-[(dimethylamino) methylene]-3,4-dihydro-7-methyl-1H-benzazepine-2,5-dione and cyclopropanecarboxamidine hydrochloride. Yield: 88%.
White solid, m/z (ISP) 266 (MH).

b) 6-Cyclopropyl-3-methyl-9H-imidazo[1,5-a]pyrimido[5,4-d][1]benzazepine-10-carboxylic Acid Ethyl Ester From 2-cyclopropyl-5,7-dihydro-10-methyl-6H-pyrimido [5,4-d][1]benzazepin-6-one according to scheme 1, step 7.
White solid, mp 250° C., m/z (ISP) 361 (MH).

The following compounds have been prepared in accordance with scheme 3:

Alternative Method to Example 1

9H-Imidazo[1,5-a]pyrimido[5,4-d][1]benzazepine-10-carboxylic Acid Ethyl Ester a) 3,4-Dihydro-1(2H)-naphthaleone (E and Z)-oxime (Compound of Formula XVII, Step 1)

A mixture of α-tetralone (13.4 mL), hydroxylamine hydrochloride (7.86 g) sodium acetate (4.39 g), water (80 mL) and ethanol (80 mL) was heated under reflux for 20 mins. The mixture was then cooled to 0° C. with and ice-MeOH bath and after 1 h, the solid was filtered off, washed with water: EtOH (1:1, 100 mL) and the solid dried under high vacuum to, give the product as white crystals (7.6 g, 47%), m/z 161 (M).

b) 1,3,4,5-Tetrahydro-2H-1-benzazepin-2-one (Compound of Formula XVIII, Step 1')

The reaction can be repeated as reported in the literature (W-Y. Chen and N. W. Gilman, Heterocycles, 1983, 663–666).

Trichloro acetic acid (502 g) was melted in a water bath and then α-tetralone (50 g) was added. To this solution was added sodium azide (33.4 g) over 90 min, with occasional cooling in ice and warming to melt the solvent. The resulting mixture was then stirred at rt for 2 h. Then the resulting mixture was heated at 70° C. for 16 h. After cooling the mixture was added to water (1 L) and then solid sodium hydrogen carbonate (400 g) was added. Then the mixture was filtered and the filtrate was extracted with DCM (4×150 mL), the combined extracts were then dried and evaporated and the solid obtained was recrystallized from EtOH to give the product (26.4 g, 48%) as white crystals, m/z 161 (M).

b) b') 1,3,4,5-Tetrahydro-2H-1-benzazepin-2-one Compound of Formula XVIII, Step 2)

The product of Step 1 (108.6) was added, over 20 mins, to a solution of polyphosphoric acid at 120° C. and the resulting mixture was then heated at 120° C. for 30 mins. After cooling, the mixture was poured into ice-water (1 L) and after 1 h, a precipitate formed and was filtered off and then dried under high vacuum at 70° C. to give the product as white crystals (94.8 g, 87%), m/z 161 (M).

c) 3,4-Dihydro-1H-1-benzazepine-2,5-dione (Compound of Formula IXX, Step 3)

The lactam (82.4 g) was dissolved in BuOH (1 L) and water (3 L) added. Then potassium permanganate (315 g) vas added followed by magnesium nitrate hexahydrate (510 g) and the mixture stirred in a water bath at rt for 48 h. Then the mixture was acidified with HCl (3 M, 7.45 mL) and then sodium bisulfite was added until the solution became yellow-orange. This mixture was extracted with DCM (3×1 L), and the combined extracts washed with water (1 L) and then dried and evaporated to give a brown solid. This was recrystallized from EtOAc to give beige crystals (30.9 g, 34%).

d) 4-[(Dimethylamino)Methylene]-3,4-dihydro-1H-benzazepine-2,5-dione (Compound of Formula XI, Step 4)

As described for compound of formula XI in step 5, scheme 1.

e) 5,7-Dihydro-6H-pyrimido[5,4-d][1]benzazepin-6-one (Compound of Formula II, Step 5)

Analogous to Scheme 1, step 6 from 4-[(dimethylamino) methylene]-3,4-dihydro-1H-benzazepine-2,5-dione and formadine acetate.

f) 9H-imidazo[1,5-a]pyrimido[5,4-d][1]benzazepine-10-carboxylic Acid Ethyl Ester (Compound of Formula I, Example 1, Step 6)

To a solution of the product from step 5 (2.2 g) in CHCl$_3$ (15 mL) was added N,N-dimethyl-p-toluidine (10.3 mL) and POCl$_3$ (1.59 mL) and the resulting mixture heated under reflux for 1 h. After cooling, the mixture was poured into a solution of NaHCO$_3$ (8.2 g) in water (40 mL), and the resulting mixture was extracted with DCM (4×20 mL) and the combined extracts were then washed with water (40 mL), dried and evaporated to give the imino chloride. To a solution of ethyl isocyanoacetate (1.19 g) in dry DMF (20 mL) was added potassium tert-butoxide (1.26 g) and the resulting solution was added to a solution of the imino chloride (prepared as above) in dry DMF (5 mL) at −50° C. After 10 mins the reaction was allowed to warm up to room temperature (40 mins) and then acetic acid (0.5 mL) was added followed by ice-cold water (200 mL). The resulting, mixture was extracted with DCM (4×40 mL) and the combined extracts washed as with water (50 mL) and then dried over MgSO$_4$ and evaporated. Chromatography of the residue on silica gel eluting with EtOAc: Hexane afforded the product (777 mg, 24%) as white crystals, m/z 306 (M).

EXAMPLE 29

6-Methyl-9H-imidazo[1,5-a]pyrimido[5,4-d][1]benzazepine-10-carboxylic Acid Ethyl Ester a) 5,7-Dihydro-2-methyl-6H-pyrimido[5,4-d]benzazepin-6-one Analogous to Scheme 1, from 4-[(dimethylamino)methylene]-3,4-dihydro-1H-benzazepine-2,5-dione and acetamidine hydrochloride. Yield: 44%.
White solid, m/z 225 (M).

b) 6-Methyl-9H-imidazo[1,5-a]pyrimido [5,4-d][1]benzazepine-10-carboxylic Acid Ethyl Ester From 5,7-dihydro-2-methyl-6H-pyrimido[5,4-d][1]benzazepin-6-one according to scheme 1, step 7.
White solid, mp 253–254° C., m/z 320 (M).

EXAMPLE 30

6-Phenyl-9H-imidazo[1,5-a]pyrimido[5,4-d][1]benzazepine-10-carboxylic Acid Ethyl Ester a) 5,7-Dihydro-2-phenyl-6H-pyrimido[5,4-d][1]benzazepin-6-one Analogous to Scheme 1, them 4-[(dimethylamino)methylene]-3,4-dihydro-1H-benzazepine-2,5-dione and benzamidine hydrochloride. Yield: 83%.
White solid, m/z 287 (M).

b) 6-Phenyl-9H-imidazo[1,5-a]pyrimido[5,4-d][1]benzazepine-10-carboxylic Acid Ethyl Ester From 5,7-dihydro-2-phenyl-6H-pyrimido[5,4-d][1]benzazepin-6-one according to scheme 1, step 7.
White solid, mp 244–246° C., m/z 382 (M).

EXAMPLE 31

6-Methyl-9H-imidazo[1,5-a]pyrimido[5,4-d][1]benzazepine-10-carboxylic Acid

To a solution of 6-methyl-9H-imidazo[1,5-a]pyrimido[5,4-d][1]benzazepine-10-carboxylic acid ethyl ester (1.6 g, 5 mmol) in EtOH (20 mL) was added sodium hydroxide (0.22 g, 5.5 mmol) and water (3.5 mL) and the resulting mixture was heated under reflux for 20 min. The mixture was then cooled to 0° C. and then hydrochloric acid (4 N, 1.32 mL) was added and the mixture was cooled in an ice-bath for 1 h. A solid formed and was filtered off and then dried under vacuum to leave the product (1.1 g, 77%) as off-white crystals, mp 285–287° C., m/z 292 (M).

EXAMPLE 32

10-(3-Cyclopropyl-1,2,4-oxadiazol-5-yl)-6-methyl-9H-imidazo[1,5-a]pyrimido[5,4-d][1]benzazepine To a suspension of 6-methyl-9H-imidazo[1,5-a]pyrimido[5,4-d][1]benzazepine-10-carboxylic acid (1.0 g, 3.4 mmol) in DMF (15 mL) was added 1,1'-carbonyldiimidazole (0.61 g, 3.76 mmol) followed by N-hydroxy-cyclopropanecarboxamidine and the resulting solution was heated at 85° C. for 1.5 h. Then acetic acid (3.4 mL) was added and the resulting mixture heated at 130° C. for 40 min. After cooling, the mixture was evaporated and dissolved n DCM (15 mL). This DCM extract was washed with sodium hydrogen carbonate (saturated solution, 40 mL) and then the aqueous phase was washed with DCM (20 mL). The combined DCM layers were then dried over MgSO$_4$ and evaporated. The residue was recrystallized from ethyl acetate: hexane to afford the product (720 mg, 59%) as white crystals, mp 216–218° C., m/z 356 (M).

EXAMPLE 33

2,3,6-Trimethyl-9H-imidazo[1,5-a]pyrimido[5,4-d][1]benzazepine-10-carboxylic Acid Ethyl Ester a) 4-[(Dimethylamino)Methylene]-3,4-dihydro-7,8-dimethyl-1H-benzazepine-2,5-dione (Compound of Formula XI)

From 3,4-dihydro-7,8-dimethyl-1H-benzazepine-2,5-dione (compound of formula X) in accordance with scheme 1 step 5.
Yield: 84%. White solid, m/z 258 (M).

b) 5,7-Dihydro-2,9,10-trimethyl-6H-pyimido[5,4-d]benzazepine-6-one (Compound of Formula II)

Analogous to Scheme 1, from 4-[(dimethylamino)methylene]-3,4-dihydro-7,8-dimethyl-1H-benzazepine-2,5-dione and acetamidine hydrochloride. Yield: 88%.
White solid, m/z 253 (M).

c) 2,3,6-Trimethyl-9H-imidazo[1,5-a]pyrimido[5,4-d][1]benzazepine-10-carboxylic Acid Ethyl Ester (Compound of Formula I)

From 5,7-dihydro-2,9,10-trimethyl-6H-pyrimido[5,4-d]benzazepine-6-one according to scheme 1, step 7.
White solid, mp 210° C., m/z 348 (M).

EXAMPLE 34

2,3-Dimethyl-6-propyl-9H-imidazo[1,5-a]pyrimido[5,4-d][1]benzazepine-10-carboxylic Acid Ethyl Ester a) 5,7-Dihydro-9,10-dimethyl-2-propyl-6H-pyrimido[5,4-d]benzazepine-6-one Analogous to Scheme 1, from 4-[(dimethylamino)methylene]-3,4-dihydro-7,8-dimethyl-1H-benzazepine-2,5-dione and butyramidine hydrochloride. Yield: 67%.
White solid, m/z (ISP) 2,82 (MH).

b) 2,3-Dimethyl-6-propyl-9H-imidazo,[1,5-a]pyrimido[5,4-d][1]benzazepine-10-carboxylic Acid Ethyl Ester From 5,7-dihydro-9,10-dimethyl-2-propyl-6H-pyrimido[5,4-d]benzazepine-6-one according to scheme 1, step 7.
White solid, mp 213° C., m/z 376 (M).

EXAMPLE 35

6-[(4-Methoxyphenyl)Methyl)-2,3-dimethyl-9H-imidazo[1,5-a]pyrimido[5,4-d][1]benzazepine-10-carboxylic Acid Ethyl Ester a) 5,7-Dihydro-2-[(4-methoxyphenyl)Methyl]-9,10-dimethyl-6H-pyrimido[5,4-d]benzazepine-6-one Analogous to Scheme 1, from 4-[(dimethylamino)methylene]-3,4-dihydro-7,8-dimethyl-1H-benzazepine-2,5-dione and 2-(4-methoxyphenyl)-acetamidine hydrochloride. Yield: 79%.
White solid, m/z (ISP) 360 (MH).

b) 6-[(4-Methoxyphenyl)Methyl]-2,3-dimethyl-9H-imidazo[1,5-a]pyrimido[5,4-d][1]benzazepine-10-carboxylic Acid Ethyl Ester From 5,7-dihydro-2-[(4-methoxyphenyl)methyl]-9,10-dimethyl-6H-pyrimido[5,4-d]benzazepine-6-one according to scheme 1, step 7.
White solid, mp 150° C., m/z (ISP) 455 (MH).

EXAMPLE 36

6-(1H-indol-3-yl-methyl)-2,3-dimethyl-9H-imidazo[1,5-a]pyrimido[5,4-d][1]benzazepine-10-carboxylic Acid Ethyl Ester a) 5,7-Dihydro-2-[1H-indol-3-yl-methyl]9,10-dimethyl-6H-pyrimido[5,4-d]benzazepine-6-one Analogous to Scheme 1, from 4-[(dimethylamino)methylene]-3,4-dihydro-7,8-dimethyl-1H-benzazepine-2,5-dione and 2-(1H-indol-3-yl)-acetamidine. Yield: 72%.
White solid, m/z 368 (M).

b) 6-(1H-indol-3-yl-methyl)-2,3-dimethyl-9H-imidazo[1,5-a]pyrimido[5,4-d][1]benzazepine-10-carboxylic Acid Ethyl Ester From 5,7-dihydro-2-[1H-indol-3-yl-methyl]-9,10-dimethyl-6H-pyrimido[5,4-d]benzazepine-6-one according to scheme 1, step 7.
White solid, mp 135° C., m/z (ISP) 464 (MH).

EXAMPLE 37

2-Bromo-11-methyl-7-(5-methyl-isoxazol-3-yl)-8H-4b,6,10,12-tetraaza-dibenzo[e,g]Azulene a) 5-Methyl-isoxazole-3-carboxylic Acid Ethyl Ester To a solution of ethyl-2,4-dioxovalerate (20 g, 126 mmol) in ethanol (85 mL), was added hydroxylamine hydrochloride (8.8 g, 126 mmol) and sodium hydrogen carbonate (10.6 g, 0.126 mmol). The reaction mixture was then heated under reflux for 1 hour. After cooling, the mixture was evaporated to leave a clear liquid that was distilled to leave the title compound as a colorless liquid (13.3 g, 68%); m/z (EI) 156.0 (MH).

b) (5-Methyl-isoxazol-3-yl)-methanol

To a solution of 5-methyl-isoxazole-3-carboxylic acid ethyl ester (13.3 g, 86 mmol) in ethanol (175 mL) under argon at 0° C. was added portion wise NaBH$_4$ (8.8 g, 231 mmol) over 30 minutes. The reaction was allowed to warm up to rt. After 3 h the reaction mixture was diluted with HCl (1 M, 100 mL) and then after cooling to room temperature the mixture was washed with ether (2×250 mL), the combined extracts dried and evaporated to leave the title compound as a colorless oil (8.1 g, 84%). m/z (EI) 113.0 (M).

c) 3-Bromomethyl-5-methyl-isoxazole

To a solution of PBr$_3$ (1.4 g, 25 mmol) and pyridine (0.5 mL) in Toluene (12 mL) was added at −10° C. a solution of hydroxymethyl-3-methyl-5-isoxazole (2.8 g, 25 mmol) in pyridine (0.2 mL). The reaction mixture was then stirred at −10° C. for 1 h and stirred for 14 h at rt. Then, the reaction mixture was diluted with water (50 mL) and extracted with ether (2×50 mL). The combined extracts were then dried and evaporated. The residue was purified by chromatography over silica gel eluting with EtOAc/Hexane 1:9 afforded the title compound as a colorless liquid (1.7 g 39%). m/z (EI) 175.0/177.0 (M).

d) 3-Azidomethyl-5-methyl-isoxazole

To a solution of the 3-bromomethyl-5-methyl-isoxazole (150 mg, 0.9 mmol) in acetone (1 mL) was added NaN$_3$ (166 mg, 0.26 mmol) at rt. The reaction mixture was then stirred for 48 h. Then, the reaction mixture was poured into water (10 mL) and extracted with EtOAc (3×10 mL) dried and evaporated. The product was chromatographed on silica gel eluting with EtOAc/hexane 1:1 to leave the title compound as a colorless liquid (87 mg, 74%). m/z 138.0 (M).

e) (5-Methyl-isoxazol-3-yl)-methylamine

To a solution of the 3-azidomethyl-5-methyl-isoxazole (6.2 g, 44.55 mmol) in isopropanol (100 mL) at rt with vigorous stirring was added triethylamine (12.4 mL, 89.0 mmol), 1,3 propanedithiol (0.45 mL, 4.5 mmol)) and sodium borohydride (1.7 g, 44.5 mmol). The mixture was then stirred at rt. After 19 hours 0.5 eq more of NaBH$_4$ (850 mg, 44.5 mmol) was added and stirred at rt for 7 hours more. Then the solvent was evaporated under vacuum and the residue was then dissolved in 10% aqueous citric acid (10 mL) and washed with ether/hexane 1:1 (3×150 mL). The aqueous layer was basified with aqueous NaOH 6 N until pH 12, saturated with NaCl, and extracted with DCM (4×200 mL) The combined DCM extracts were dried and concentrated to leave the title compound as a colorless liquid (4.4 g, 87%). m/z 112.0 (M).

f) N,N-Dimethyl-N'-(5-methyl-isoxazol-3-yl-methyl)-formamidine

A solution of the C-(5-methyl-isoxazol-3-yl)-methylamine (150 mg, 1.3 mmol) in N,N-dimethylformamide dimethylacetal (2 mL, 14.4 mmol) was heated under reflux for 3 h. After cooling to room temperature, the solvent was evaporated to leave the title compound as a yellow oil (220 mg, 98%. m/z 168.2 (MH)

g) 2-Bromo-11-methyl-7-(5-methyl-isoxazol-3-yl)-8H-4b,6,10,12-tetraaza-dibenzo[e,g]Azulene From 10-bromo-5,7-dihydro-2-methyl-6H-pyrimido[5,4-d][1]benzazepin-6-one according to scheme 1, step 7 using N,N-dimethyl-N'-(5-methyl-isoxazol-3-ylmethyl)-formamidine instead of (E)-(dimethylaminomethyleneamino)-acetic acid ethyl ester. Clear gum, m/z (ISP) 407/409 (MH)

Alternative Rotates without Purification of Intermediate 2-[(4-Ethoxy-1,4-dioxobutyl)Amino)]-benzoic Acid Ethyl Ester (Compound of Formula VIII)

To a stirred solution of ethyl anthranilate (5.0 g) in dry toluene (25 mL) at 0° C. was added calcium carbonate (6.1 g) followed by a solution of ethyl succinyl chloride (6.0 g) in dry toluene (40 mL) and the reaction mixture allowed to warm up to rt over 30 mins. The resulting mixture was then heated under reflux for 1 h and then the hot suspension was filtered. The solution was then evaporated to leave a white solid (8.9 g, 100%) as white crystals, m/z 293 (M).

2,3-Dihydro-5-hydroxy-2-oxo-1H-benzazepine-4-carboxylic Acid Ethyl Ester (Compound of Formula IX)

To a suspension of NaH in oil (0.5 g) was added THF (30 ml) under Argon. To this suspension at rt was added the product of step 2 as a solution in THF (5 mL), over 5 min. After hydrogen evolution had stopped, the resulting mixture was heated at 70° C. for 15 min. After cooling, acetic acid (1 mL) was added with stirring followed by the addition of water (120 mL). The mixture was then filtered and the solid obtained was dried in the vacuum oven at 60° C. at 10 mbar, for I h to give a white solid (0.8 g, 99%), m/z 247(M).

3,4-Dihydro-1H-1-benzazepine-2,5-dione (Compound of Formula X)

The product of step 3 (0.8 g) was dissolved in DMF (30 mL) and then NaCl (0.28 g) and water (0.11 mL) was added and the resulting mixture heated under reflux for 3 h. After cooling, the mixture was then extracted with DCM (3×5 ml), the combined extracts washed with water (10 mL), then dried and evaporated to leave an off-white orange solid. Recrystallization from EtOH afforded an off-white solid (0.54 g, 95%), m/z 175 (M).

Preparation of Intermediates in Accordance with Scheme 4

4-(2-Nitro-phenyl)-4-trimethlysilanyloxy-butyric Acid Ethyl Ester (Compound of Formula XXI)

To a suspension of freshly fused zinc iodide (5.28 g, 16.5 mmol) in dry DCM (2 mL) under Argon at room temperature was added a solution of 2-nitrobenzaldehyde (5.0 g, 33.0 mmol) and (1-ethoxycyclopropyloxy)trimethylsilane (7.50 g, 43.0 mmol) in dry DCM (20 mL) over 5 mins. After 1.5 h, hydrochloric acid (1 M, 50 mL) was added to the reaction mixture and the resulting mixture was extracted with DCM (3×50 mL). The combined organic extracts were dried over sodium sulfate and evaporated to leave an oil. Purification by chromatography on silica gel, eluting with hexane: ethyl acetate (9:1) afforded the title compound (8.3 g, 77%) as a colorless oil; m/z 324 (M). 4-Hydroxy-4-(2-nitro-phenyl)-butyric acid ethyl ester was isolated as a side product of the reaction. [Yield: 10%, m/z 254 (MH)]

4-(2-Nitro-phenyl)-4-oxo-butyric Acid Ethyl Ester (Compound of Formula XXII)

To a solution of 4-(2-nitro-phenyl)-4-trimethlysilanyloxy-butyric acid ethyl ester (530 mg, 1.6 mmol) in dry DCM (5 mL) under Argon was added PCC (pyridinium chlorochromate) (878 mg, 4.1 mmol) and the resulting mixture stirred vigorously for 20 h. Then silica gel (5 g) was added and the mixture filtered. The filtrate was then evaporated and the residue purified by chromatography on silica gel, eluting with ethyl acetate: hexane (3:1) to afford the title compound (375 mg, 92%) as a colorless liquid; m/z 252 (MH).

4-(2-Amino-phenyl)-4-oxo-butyric Acid Ethyl Ester (Compound of Formula XXIII)

Method 1

A solution of 4-(2-nitro-phenyl)-4-oxo-butyric acid ethyl ester (200 mg, 0.8 mmol) in dry MeOH (5 mL) in the presence of Pd/C (20 mg) was hydrogenated (1 atm) for 3 h. The mixture was then filtered and the filtrate evaporated. Purification by filtration over silica gel, eluting with DCM afforded the title compound (140 mg, 80%) as a colorless oil; m/z 222 (MH).

Method 2

To a solution of 4-hydroxy-4-(2-nitro-phenyl)-butyric acid ethyl ester (200 mg, 0.9 mmol) in dry DCM (10 mL) was added 4-methylmorpholine N-oxide (157.4 mg, 1.3 mmol) and tetrapropylammonium perruthenate (31.5 mg, 0.09 mmol) and the resulting mixture stirred at room temperature for 1 h. Then the mixture was filtered and washed with ether. Purification of this residue by filtration over silica gel, eluting with DCM afforded the title compound (107 mg, 54%) as a colorless oil; m/z 222 (MH).

Method 3

To a solution of 4-(2-amino-phenyl)-4-trimethlysilanyloxy-butyric acid ethyl ester (200 mg, 0.7 mmol) in dry DCM (10 mL) was added 4-methylmorpholine N-oxide (157.4 mg, 1.3 mmol) and tetrapropylammonium perruthenate (31.5 mg, 0.09 mmol) and the resulting mixture stirred at room temperature for 1 h. Then the mixture was filtered and washed with ether. Purification of this residue by filtration over silica gel, eluting with DCM afforded the title compound (84 mg, 54%) as a colorless oil; m/z 222 (MH).

4-(2-Amino-phenyl)-4-trimethlysilanyloxy-butyric Acid Ethyl Ester (Compound of Formula XXVI)

A solution of 4-(2-nitro-phenyl)-4-trimethlysilanyloxy-butyric acid ethyl ester (200 mg, 0.6 mmol) in dry EtOAc (5 mL) was hydrogenated (1 atm) in the presence of Pd/C (20 mg) overnight Then the mixture was filtered and evaporated. The residue was dissolve in dry MeOH (5 mL) and was further hydrogenated (1 atm) in the presence of Pd/C (20 mg) for 1 h. The mixture was then filtered and the filtrate evaporated. Purification of this residue by filtration over silica gel, eluting with hexane: ethyl acetate (8:1) afforded the title compound (130 mg, 72%) as a colorless oil; m/z 295 (M).

4-(2-Amino-phenyl)-4-hydroxy-butyric Acid Ethyl Ester (Compound of Formula XXV)

Method 1

A solution of 4-hydroxy-4-(2-nitro-phenyl)-butyric acid ethyl ester (200 mg, 0.8 mmol) in dry MeOH (5 mL) was hydrogenated (1 atm) in the presence of Pd/C (20 mg) for 5 h. The mixture was then filtered and the filtrate evaporated. Purification of this residue by filtration over silica gel, eluting with ethyl acetate: hexane (3:1) afforded the title compound (100 mg, 57%) as a colorless oil; m/z 224 (M).

Method 2

A solution of 4-(2-nitro-phenyl)-4-trimethlysilanyloxy-butyric acid ethyl ester (200 mg, 0.6 mmol) in dry MeOH (5 mL) with a few drops of ethyl acetate was hydrogenated (1 atm) in the presence of Pd/C (20 mg) for 20 h. The mixture was then filtered and the filtrate evaporated. Purification of this residue by filtration over silica gel, eluting with DCM: ethyl acetate (8:1) afforded the title compound (115 mg, 84%) as a colorless oil; m/z 224 (M).

3,4-Dihydro-1H-1-benzazepine-2,5-dione (Compound of Formula X)

To a suspension of sodium hydride (10 mg, 0.43 mmol) in dry THF (1 mL) was added 4-(2-amino-phenyl)-4-oxo-butyric acid ethyl ester (80 mg, 0.36 mmol) under Argon at −40° C. The reaction mixture was then allowed to warm up to rt over 3 h, and then added to water (20 mL). The mixture was then extracted with DCM (3×15 mL) and the combined extracts were then dried (sodium sulfate), and evaporated to leave an off-white solid. Recrystallization from EtOAc afforded a white solid (51 mg, 81%), m/z 175 (M).

In the examples A, B and C below, the term "active substance" refers to a compound of Formula I, or pharmaceutically acceptable salt thereof.

EXAMPLE A

Tablets of the following composition are manufactured in the usual manner:

| mg/tablet | |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| mg/capsule | |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting, machine. The mixture is returned to the mixer, the talc is added thereto and mixed thoroughly. The mixture is filled by machine into hard gelatin capsules.

EXAMPLE C

Suppositories of the following composition are manufactured:

| mg/supp. | |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository molds of suitable size, left to cool, the suppositories are then removed from the molds and packed individually in wax paper or metal foil.

What is claimed is:

1. A compound of formula:

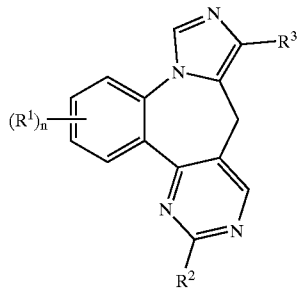

wherein
- $R^1$ is selected from the group consisting of halogen and lower alkyl;
- $R^2$ is selected from the group consisting of hydrogen, lower alkyl, cycloalkyl, —$(CH_2)_m$-phenyl, —$(CH_2)_m$-phenyl substituted by lower alkoxy and —$(CH_2)_m$-indolyl;
- $R^3$ is selected from the group consisting of —(O)O-lower alkyl, —C(O)OH, an unsubstituted five-membered heteroaromatic group and a five-membered heteroaromatic group substituted by lower alkyl or cycloalkyl;
- n is 0, 1 or 2; and
- m is 0, 1 or 2;

or a pharmaceutically acceptable acid addition salt thereof.

2. A compound of formula I according to claim 1, wherein $R^3$ is an unsubstituted five-membered heteroaromatic group or a five-membered heteroaromatic group substituted by cycloalkyl.

3. A compound of formula I according to claim 1, in which $R^3$ is the group —C(O)O-lower alkyl and n is 0.

4. A compound of formula I according to claim 3 selected from the group consisting of:
   9H-imidazo[1,5-a]pyrimido[5,4-d][1]benzazepine-10-carboxylic acid ethyl ester,
   6-propyl-9H-imidazo[1,5-a]pyrimido[5,4-d][1]benzazepine-10-carboxylic acid ethyl ester,
   6-(1-methylethyl)-9H-imidazo[1,5-a]pyrimido[5,4-d][1]benzazepine-10-carboxylic acid ethyl ester,
   6-cyclopropyl-9H-imidazo[1,5-a]pyrimido[5,4-d][1]benzazepine-10-carboxylic acid ethyl ester,
   6-[(4-methoxyphenyl)methyl]-9H-imidazo[1,5-a]pyrimido[5,4-d][1]benzazepine-10-carboxylic acid ethyl ester and
   6-methyl-9H-imidazo[1,5-a]pyrimido[5,4-d][1]benzazepine-10-carboxylic acid ethyl ester.

5. A compound of formula I according to claim 1, wherein $R^3$ is the group —C(O)O-lower alkyl and $R^1$ is halogen.

6. A compound of formula I according to claim 5 selected from the group consisting of:
   3-fluoro-6-methyl-9H-imidazo[1,5-a]pyrimido[5,4-d][1]benzazepine-10-carboxylic acid ethyl ester,
   3-fluoro-6-propyl-9H-imidazo[1,5-a]pyrimido[5,4-d][1]benzazepine-10-carboxylic acid ethyl ester,
   3-fluoro-6-(1-methylethyl)-9H-imidazo[1,5-a]pyrimido[5,4-d][1]benzazepine-10-carboxylic acid ethyl ester,
   6-cyclopropyl-3-fluoro-9H-imidazo[1,5-a]pyrimido[5,4-d][1]benzazepine-10-carboxylic acid ethyl ester and
   3-bromo-6-methyl-9H-imidazo[1,5-a]pyrimido[5,4-d][1]benzazepine-10-carboxylic acid ethyl ester.

7. A compound of formula I according to claim 1, wherein $R^3$ is selected from the group consisting of unsubstituted 1,2,4-oxadiazolyl, unsubstituted isoxazolyl and 1,2,4-oxadiazolyl or isoxazolyl substituted by lower alkyl or cycloalkyl, $R^2$ is lower alkyl, n is 0 or 1 and $R^1$ is halogen.

8. A compound of formula I according to claim 7 selected from the group consisting of 10-(3-cyclopropyl-1,2,4-oxadiazol-5-yl)-6-methyl-9H-imidazo[1,5-a]pyrimido[5,4-d][1]benzazepine and
   2-bromo-11-methyl-7-(5-methyl-isoxazol-3-yl)-8H-4b,6,10,12-tetraaza-dibenzo[e,g]azulene.

9. A pharmaceutical composition comprising a therapeutically effective amount of at least one compound of formula I, as defined in claim 1, or a pharmaceutically acceptable salt thereof, and at least one pharmaceutically acceptable excipient.

10. A process for preparing a compound of formula I, as defined in claim 1, comprising:

a) reacting a compound of formula:

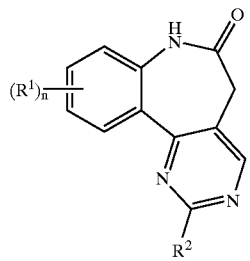

II with phosphoroxychloride,
forming a compound of formula:

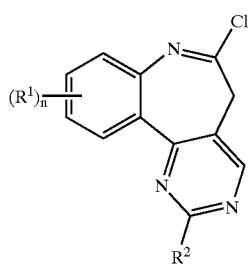

III wherein the substituents $R^1$ and $R^2$ and n have are as defined in claim 1, and reacting this compound with:

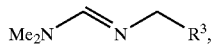

IV forming a compound of formula:

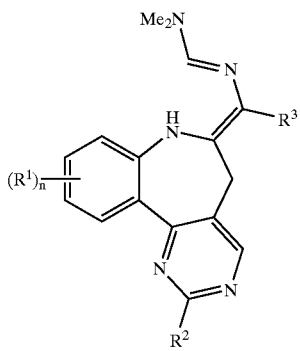

V and cyclizing this compound with:

MeCO$_2$H, thereby forming a compound of formula:

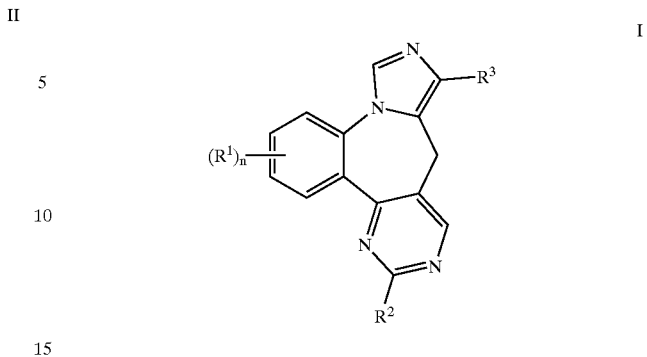

I wherein $R^1$, $R^3$ and n are as defined in claim 1.

11. A process for preparing a compound of formula I, as defined in claim 1, comprising:

reacting a compound of formula:

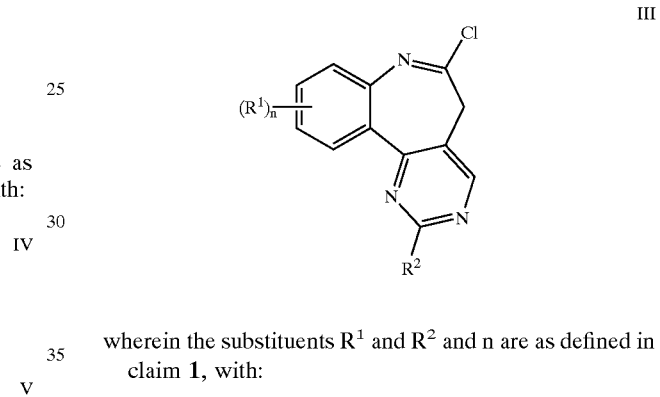

III wherein the substituents $R^1$ and $R^2$ and n are as defined in claim 1, with:

N≡C—R$^3$,

IVa forming a compound of formula I, and converting the compound obtained into a pharmaceutically acceptable acid addition salt.

12. A method of treatment of Alzheimer's disease comprising administering a therapeutically effective amount of a compound of formula I, as defined in claim 1, or a pharmaceutically acceptable salt thereof, to a person in need of such treatment.

* * * * *

UNITED STATES PATENT AND TRADEMARK OFFICE
CERTIFICATE OF CORRECTION

PATENT NO. : 6,686,352 B2
DATED : February 3, 2004
INVENTOR(S) : Raffaello Masciadri, Andrew William Thomas and Juergen Wichmann It is certified that error appears in the above-identified patent and that said Letters Patent is hereby corrected as shown below:

Column 33,
Line 66, "-(O)O-lower" should read -- -C(O)O-lower --.

Signed and Sealed this

Twenty-second Day of June, 2004

JON W. DUDAS
*Acting Director of the United States Patent and Trademark Office*